US006417204B1

(12) United States Patent
Haque

(10) Patent No.: US 6,417,204 B1
(45) Date of Patent: Jul. 9, 2002

(54) PYRIDOXINE AMD PYRIDOXAL ANALOGUES: CARDIOVASCULAR THERAPEUTICS

(75) Inventor: Wasimul Haque, Edmonton (CA)

(73) Assignee: Medicure International Inc., St. James (BB)

( * ) Notice: Subject to any disclaimer, the term of this patent is extended or adjusted under 35 U.S.C. 154(b) by 0 days.

(21) Appl. No.: 09/900,718

(22) Filed: Jul. 6, 2001

Related U.S. Application Data

(60) Provisional application No. 60/216,907, filed on Jul. 7, 2000.

(51) Int. Cl.$^7$ ................ C07D 401/02; A61K 31/44
(52) U.S. Cl. ................ 514/340; 514/341; 514/357; 546/272.4; 546/272.7; 546/268.4; 546/300
(58) Field of Search .............. 546/272.4, 272.7, 546/268.4, 300; 514/340, 341, 357

(56) References Cited

U.S. PATENT DOCUMENTS

| | | | |
|---|---|---|---|
| 3,206,463 A | 9/1965 | Baetz | 546/300 |
| 3,910,921 A | 10/1975 | Esanu | 260/286 |
| 3,987,177 A | 10/1976 | Giudicelli et al. | 260/286 |
| 4,032,534 A | 6/1977 | Chodkiewicz | 260/306.7 |
| 4,036,844 A | 7/1977 | Thorne et al. | 260/295 |
| 4,053,607 A | 10/1977 | Thorne et al. | 424/263 |
| 4,137,316 A | 1/1979 | Esanu | 424/256 |
| 4,167,562 A | 9/1979 | Evers | 424/153 |
| 4,361,570 A | 11/1982 | Fici | 424/263 |
| 4,369,172 A | 1/1983 | Schor et al. | 424/19 |
| 4,374,841 A | 2/1983 | Descamps et al. | 424/263 |
| 4,515,771 A | 5/1985 | Fine | 424/52 |
| 4,567,179 A | 1/1986 | Lombardino | 514/225 |
| 4,569,938 A | 2/1986 | Esanu | 514/302 |
| 4,569,939 A | 2/1986 | Esanu | 514/302 |
| 4,581,363 A | 4/1986 | Esanu | 514/302 |
| 4,605,741 A | 8/1986 | Zagnoli et al. | 546/24 |
| 4,696,920 A | 9/1987 | Bentzen et al. | 514/89 |
| 4,730,042 A | 3/1988 | Hege et al. | 544/124 |
| 4,735,950 A | 4/1988 | Esanu | 514/262 |
| 4,735,956 A | 4/1988 | Baldwin et al. | 514/338 |
| 4,837,239 A | 6/1989 | Benjamin et al. | 514/267 |
| 4,843,071 A | 6/1989 | Hohenwarter | 514/217 |
| 4,962,121 A | 10/1990 | Hamberger et al. | 514/419 |
| 5,001,115 A | 3/1991 | Sloan | 514/34 |
| 5,053,396 A | 10/1991 | Blass | 514/45 |
| 5,118,505 A | 6/1992 | Költringer | 424/195.1 |
| 5,130,324 A | 7/1992 | Ulrich et al. | 514/357 |
| 5,132,115 A | 7/1992 | Wolter et al. | 424/448 |
| 5,210,083 A | 5/1993 | Pfirrmann | 514/222.5 |
| 5,213,813 A | 5/1993 | Kornecki et al. | 424/532 |
| 5,254,557 A | 10/1993 | Buckle et al. | 514/269 |
| 5,254,572 A | 10/1993 | Serfontein | 514/345 |
| 5,272,165 A | 12/1993 | Ulrich et al. | 514/357 |
| 5,278,154 A | 1/1994 | Lacoste et al. | 514/114 |
| 5,288,716 A | 2/1994 | Speck | 514/89 |

(List continued on next page.)

FOREIGN PATENT DOCUMENTS

| | | |
|---|---|---|
| BE | 831350 | 1/1976 |
| BE | 863754 | 5/1978 |
| CH | 561 183 | 4/1975 |
| DE | 1 958 226 | 5/1970 |
| DE | 24 61 742 A | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1323941 | 12/1963 |
| FR | 5552 M | 12/1967 |
| FR | 5801 M | 3/1968 |
| FR | 6453 M | 12/1968 |
| FR | 1579544 | 8/1969 |
| FR | 2 034 539 | 12/1970 |
| FR | 2101010 | 3/1972 |
| FR | 2255883 | 7/1975 |
| FR | 2428640 | 1/1980 |
| GB | 1 013 939 | 12/1965 |
| GB | 1172800 | 12/1969 |
| GB | 1 201 014 | 8/1970 |
| GB | 1 297 080 | 11/1972 |
| GB | 1 360 536 | 7/1974 |
| GB | 1 493 993 | 12/1977 |
| GB | 1 597 428 | 9/1981 |
| GB | 2 254 556 A | 10/1992 |
| JP | 48-21959 | 7/1973 |
| JP | 54-17130 | 2/1979 |
| JP | 10-158244 | 6/1998 |
| JP | 2000-26295 | 1/2000 |
| WO | WO 83/00085 | 1/1983 |
| WO | WO 91/19500 | 12/1991 |
| WO | WO 94/18965 | 9/1994 |
| WO | WO 98/28310 | 7/1998 |
| WO | WO 99/03365 | 1/1999 |
| WO | WO 99/53928 | 10/1999 |

OTHER PUBLICATIONS

Arbuzov, S., "Pharmacologocial Properties of the Products of the Condensation of Phenamine with Some Metabolites", Farmakol. Toksikol, vol. 31, No. 3, pp. 373–376 (1968) (Abstract only).

(List continued on next page.)

Primary Examiner—Zinna Northington Davis
(74) Attorney, Agent, or Firm—Merchant & Gould, P.C.

(57) ABSTRACT

The invention provides pyridoxal and pyridoxine analogues, pharmaceutical compositions containing pyridoxine and pyridoxal analogues, and methods of administering pharmaceutical compositions containing a therapeutically effective amount of at least one of these analogues. In accordance with the present invention, the pyridoxal and pyridoxine analogues can be used in the treatment of cardiovascular or related diseases and in the treatment of symptoms thereof.

41 Claims, No Drawings

U.S. PATENT DOCUMENTS

| | | |
|---|---|---|
| 5,326,757 A | 7/1994 | Demopoulos ............... 514/167 |
| 5,328,453 A | 7/1994 | Sibalis ......................... 604/20 |
| 5,372,999 A | 12/1994 | Schneider et al. ............ 514/81 |
| 5,385,937 A | 1/1995 | Stamler et al. ............. 514/557 |
| 5,420,112 A | 5/1995 | Lewis et al. .................. 514/12 |
| 5,441,972 A | 8/1995 | Ogata et al. ................ 514/342 |
| 5,504,090 A | 4/1996 | Neely .......................... 514/263 |
| 5,563,126 A | 10/1996 | Allen et al. .................... 514/52 |
| 5,569,459 A | 10/1996 | Shlyankevich ........... 424/195.1 |
| 5,569,648 A | 10/1996 | Lewis et al. .................. 514/12 |
| 5,631,271 A | 5/1997 | Serfontein .................. 514/345 |
| 5,633,228 A | 5/1997 | Lewis et al. .................. 514/12 |
| 5,648,335 A | 7/1997 | Lewis et al. .................. 514/12 |
| 5,728,684 A | 3/1998 | Cheng et al. ................. 514/50 |
| 5,733,884 A | 3/1998 | Barbul et al. ................. 514/21 |
| 5,733,916 A | 3/1998 | Neely ........................... 514/50 |
| 5,770,215 A | 6/1998 | Moshyedi .................... 514/21 |
| 5,795,873 A | 8/1998 | Allen .......................... 514/52 |
| 5,804,163 A | 9/1998 | Gibby et al. ............. 424/936.1 |
| 5,804,594 A | 9/1998 | Murad ........................ 514/474 |
| 5,833,998 A | 11/1998 | Biedermann et al. ....... 424/401 |
| 5,834,446 A | 11/1998 | Dow et al. .................... 514/12 |
| 5,840,685 A | 11/1998 | Fujii et al. .................. 514/708 |
| 5,847,008 A | 12/1998 | Doebber et al. ............ 514/708 |
| 5,858,017 A | 1/1999 | Demopulos et al. ..... 604/890.1 |
| 5,859,051 A | 1/1999 | Adams et al. ............... 514/469 |
| 5,874,420 A | 2/1999 | Pelleg .......................... 514/81 |
| 5,874,443 A | 2/1999 | Kiely et al. ................. 514/309 |
| 5,888,514 A | 3/1999 | Weisman ................. 424/195.1 |
| 5,944,020 A | 8/1999 | Markov et al. ............... 514/23 |
| 6,043,259 A | 3/2000 | Dhalla et al. ............... 514/345 |

OTHER PUBLICATIONS

Arbuzov, S., "Synthesis and Pharmacological Investigation of Some New Compounds Related Structurally to Some Natural Metabolites", *Conf. Hung. Ther. Invest. Pharamcol., Soc. Pharmacol. Hung., 4th Meeting*, pp. 489–502 (1966) (Abstract only).

Aybak, M. et al., "Effect of Oral Pyridoxine Hydrochloride Supplementation on Arterial Blood Pressure in Patients with Essential Hypertension", *Drug Res.*, vol. 45, No. 12, pp. 1271–1273 (1995).

"B Vitamins May Cut Heart Disease Risk", *Harvard Health Letter*, 1 page (1998).

Baliga, B. et al., "Hyperhomocysteinemia in Type 2 Diabetes Mellitus: Cardiovascular Risk Factors and Effect of Treatment with Folic Acid and Pyridoxine", *Endocrine Practice*, vol. 6, No. 6, pp. 435–441 (Nov./Dec. 2000).

Barrett, S., "Homocysteine: A Cardiovascular Risk Factor Worth Considering", http://www.quackwatch.com/03HealthPromotion/homocysteine.html, 2 pages (©1997).

Bennett, R. et al., "Vitamin $B_6$–Phosphonic Acids", *Journal of Medicinal and Pharmaceutical Chemistry*, vol. 1, No. 3, pp. 213–221 (1959).

Bernstein, A., "Vitamin $B_6$ in Clinical Neurology", *Annals of New York Academy of Sciences*, vol. 585, pp. 250–260 (1990).

Berger, A.R. et al., "Dose response, coasting, and differential fiber vulnerability in human toxic neuropathy: A prospective study of pyridoxine neurotoxicity", *Neurology*, vol. 42, No. 7, pp. 1367–1370 (Jul. 1992).

Bhagavan, H. et al., "Effect of Postweanling Pyridoxine Deficiency on Growth and Concentration of the Coenzyme Pyridoxal–5'–phosphate in Heart, Kidneys, Lungs, and Adrenals in Rats", *Pediat. Res.*, vol. 10, pp. 730–732 (1976).

Bode, W. et al., "Pyridoxal–5'–Phosphate and Pyridoxal Biokinetics in Male Wistar Rats Fed Graded Levels of Vitamins B–6", *J. Nutr.*, vol. 121, No. 11, pp. 1738–1745 (Nov. 1991).

Chasan–Taber, L. et al., "A Prospective Study of Folate and Vitamin $B_6$ and Risk of Myocardial Infarction in US Physicians", *Journal of the American College of Nutrition*, vol. 15, No. 2, pp. 136–143 (Apr. 1996).

Cho, Y. et al., "In Vivo Evidence for a Vitamin B–6 Requirement in Carnitine Synthesis", *J. Nutr.*, vol. 120, pp. 258–265 (1990).

"Computer Generated Search Reports", 70 pages (May 1999).

Ebadi, M. et al., "Convulsant Activity of Pyridoxal Sulphate and Phosphonoethyl Pyridoxal: Antagonism by GABA and its Synthetic Analogues", *Neuropharmacology*, vol. 22, No. 7, pp. 865–873 (1983).

Ellis, J. et al., "Prevention of Myocardial Infarction by Vitamin $B_6$", *Res. Commun. Molec. Pathol. Pharmacol.*, vol. 89, No. 2, pp. 208–220 (Aug. 1995).

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", *Circulation*, vol. 98, pp. 204–210 (Jul. 21, 1998).

Fonda, M., "Interaction of Pyridoxal Analogues with Glutamate Apodecarboxylase and Aspartate Apoaminotransferase", *The Journal of Biological Chemistry*, vol. 246, No. 7, pp. 2230–2240 (Apr. 10, 1971).

Gundermann, K. et al., "Oligomere von 5–Amino–8–vinylphthalazin–1,4(2H,3H)–dion", *Liebigs Ann. Chem.*, vol. 1979, No. 8, pp. 1657–1664 (Aug. 1979).

Harada, K. et al., "Studies on Vitamin $B_6$ (IV) Behavior of Pyridoxal Acylates in the Body After Parenteral Administration", *Vitamins Journal of the Vitamin Society of Japan*, vol. 45, No. 2, pp. 69–75 (Feb. 1972).

Hathcock, J., "Vitamins and minerals: efficacy and safety", *Am J Clin Nutr*, vol. 66, pp. 427–437 (1997).

Hayakawa, M. et al., "The In Vitro and In Vivo Inhibition of Protein Glycosylation and Diabetic Vascular Basement Membrane Thickening by Pyridoxal–5'–Phosphate", *J. Nutr. Sci. Vitaminol.*, vol. 37, pp. 149–159 (1991).

Hoover, D.M. et al., "Ultrastructural Lesions of Pyridoxine Toxicity in Beagle Dogs", *Vet. Pathol.*, vol 18, pp. 769–777 (1981).

Karnalitsky, I., "Comparative Biochemical Characteristic of $B_6$–Vitamin Deficiency Caused by Alimentary Insufficiency of Pyridoxine and Isonicotinylhydrazide", *BOπPOCbI*, vol. 3, pp. 44–46 (1971).

Kim, Y. et al., "Synthesis and Structure–Activity Relationships of Pyridoxal–6–arylazo–5'–phosphate and Phosphonate Derivatives as P2 Receptor Antagonists", *Drug Development Research*, vol. 45, pp. 52–66 (1998).

Kok, F. et al., "Low Vitamin $B_6$ Status in Patients with Acute Myocardial Infarction", *Am. J. Cardiol.*, vol. 63, pp. 513–516 (Mar. 1, 1989).

Korytnyk, W., "Pyridoxine Chemistry. VI. Homologs of Pyridoxol and of 5–Pyridoxic Acid", *Pyridoxine*, vol. 8, pp. 112–115 (Jan. 1965).

Korytnyk et al. Schiff Bases of Pyridoxal: Their Structure and the Stabilization of their Ring–Chain Tautomeric Forms by Acylation, Tetrahedron, 26 (23), 5415–25, 1985.

Korytnyk, W. et al., "Synthesis and Antagonist Properties of Pyridoxal Analogs Modified in the 5 Position", *Pyridoxol Analogs*, vol. 10, pp. 345–350 (May 1967).

Krinke, G. et al., "Pyridoxine Megavitaminosis: An Analysis of the Early Changes Induced with Massive Doses of Vitamin $B_6$ in Rat Primary Sensory Neurons", *J. Neuropathol. Exp. Neurol.*, vol. 44, No. 7, pp. 117–129 (Mar. 1985).

Kubyshkin, V. et al., "Comparative characteristics of the arrhythmic syndrome and the possibility for its coenzyme correction in dilated and hypertrophic cardiomyopathy", *Abstract*, 1 pg. (1989).

Lal, K. et al., "Hypotensive action of 5–HT receptor agonists in the vitamin $B_6$–deficient hypertensive rat", *Eur. J. Pharmacol.*, vol. 234, Nos. 2/3, pp. 183–189 (Apr. 1993).

Lal, K. et al., "Calcium channels in vitamin $B_6$ deficiency-induced hypertension", *Journal of Hypertension*, vol. 11, No. 12, pp. 1357–1362 (Dec. 1993).

Lal, K. et al., "The effect of vitamin $B_6$ on the systolic blood pressure of rats in various animal models of hypertension", *Journal of Hypertension*, vol. 14, No. 3, pp. 355–363 (Mar. 1996).

Levy, H. et al., "Pyridoxine Deficiency in Congestive Heart Failure", *P.S.E.B.M.*, vol. 101, pp. 617–621 (1959).

Manore, M. et al., "Changes In Plasma Pyridoxal Phosphate (PLP) In Diabetic (D), Hypertensive (HTN) and Hypertensive–diabetic (HTN–D) Men Fed A Constant Vitamin B–6 (B6) Diet", *Source Unknown*, pp. 1254 (Date Unknown).

Markov, A. et al, "Hemodynamic, electrocardiographic, and metabolic effects of fructose diphosphate on acute myocardial ischemia", *American Heart Journal*, vol. 100, No. 5, pp. 639–646 (Nov. 1980).

Mendelsohn, A. et al., "Hemodynamic and Clinical Effects of Oral Levodopa in Children With Congestive Heart Failure", *JACC*, vol. 30, No. 1, pp. 237–242 (Jul. 1997).

Merrill, Jr. et al., A. et al., "Diseases associated with defects in vitamin $B_6$ metabolism or utilization", *Ann. Rev. Nutr.*, vol. 7, pp. 137–156 (1987).

Miura, R. et al., "Reactions of Phosphonate Analogs of Pyridoxal Phosphate with Apo–aspartate Aminotransferase", *Archives of Biochemistry and Biophysics*, vol. 270, No. 2, pp. 526–540 (May 1, 1989).

Mulvaney, D. et al., "Electrocardiographic changes in vitamin $B_6$ deficient rats", *Cardiovascular Research*, vol. 13, pp. 506–513 (1979).

Nair, A. et al., "Effect of Pyridoxine and Insulin Administration on Brain Glutamate Dehydrogenase Activity and Blood Glucose Control in Streptozotocin–Induced Diabetic Rats", *Biochimica et Biophysica Acta*, vol. 1381, pp. 351–354 (1998).

Omenn, G. et al., "Preventing Coronary Heart Disease", *Circulation*, vol. 97, pp. 421–424 (1998).

Onorato, J. et al., "Pyridoxamine, an Inhibitor of Advanced Glycation Reactions, Also Inhibits Advanced Lipoxidation Reactions", *The Journal of Biological Chemistry*, vol. 275, No. 28, pp. 21177–21184 (Jul. 14, 2000).

Pasechnik, I., "Effect of Pyridoxine on the Blood Sugar Level Normally and During Experimental Hyperglycemia", *Vop. Pitan.*, vol. 30, No. 3, pp. 44–46 (Abstract only from *Chemical Abstracts—Pharmacodynamics*, vol. 75 No. 9. p. 293 (Aug. 30, 1971).

Paulose, C. et al., "Sympathetic Stimulation and Hypertension in the Pyridoxine–Deficient Adult Rat", *Hypertension*, vol. 11, No. 4, pp. 387–391 (Apr. 1988).

Rao, R. et al., "Failure of Pyridoxine to Improve Glucose Tolerance in Diabetics", *Journal of Clinical Endocrinology & Metabolism*, vol. 50, No. 1, pp. 198–200 (Jan. 1980).

Rimm, E. et al., "Folate and Vitamin $B_6$ From Diet and Supplements in Relation to Risk of Coronary Heart Disease Among Women", *JAMA*, vol. 279, No. 5, pp. 359–364 (Feb. 4, 1998).

Sakuragi, T. et al., "The Synthesis of Long Chain Fatty Acid Derivatives of the Vitamin $B_6$ Group", *J. Am. Chem. Soc.*, vol. 78, pp. 839–842 (Feb. 20, 1956).

Sasaki, H. et al., "Effect of Pyridoxal Phosphate on the Carbohydrate and Lipid Metabolism of the Patient with Diabetes Mellitus", *Niigata Igakkai Zasshi*, vol. 85, No. 3, pp. 163–169 (1971). (Abstract provided in English).

Sethi, R. et al., "Differential changes in left and right ventricular adenylyl cyclase activities in congestive heart failure", *The American Physiological Society*, vol. 272, No. 2, Part 2 of Two Parts, pp. H884–H893 (Feb. 1997).

Sethi, R. et al., "Inotropic Responses to Isoproterenol in Congestive Heart Failure Subsequent to Myocardial Infarction in Rats", *Journal of Cardiac Failure*, vol. 1, No. 5, pp. 391–399 (Dec. 1995).

Stirtan, W. et al., "Phosphonate and $\alpha$–Fluorophosphonate Analogue Probes of the Ionization State of Pyridoxal 5'–Phosphate (PLP) in Glycogen Phosphorylase", *Biochemistry*, vol. 35, pp. 15057–15064 (1996).

Takuma, Y. et al., "Combination Therapy of Infantile Spasms With High–Dose Pyridoxal Phosphate and Low–Dose Corticotropin", *Journal of Child Neurology*, vol. 11, No. 1, pp. 35–40 (Jan. 1996).

Tanaka, T. et al., "Pyridoxine Derivatives", *Chemical Abstracts*, vol. 62, No. 12, 1 page (Jun. 7, 1965).

Tomita, I. et al., "Synthesis of Vitamin $B_6$ Derivatives. II 3–Hydroxy–4–Hydroxymethyl–2–Methyl–5–Pyridine Acetic Acid and Related Substances", *Department of Biochemistry and Biophysics, Iowa State University*, vol. 3, pp. 178–183 (Jun. 1966).

Trezise, D. et al., "$P_2$ purinoceptor antagonist properties of pyridoxal–5–phosphate", *Eur. J. Pharmacol.*, vol. 259, No. 3, pp. 295–300 (Jul. 11, 1994).

Vanderjagt, D. et al., "Vitamin $B_6$ Status in a Healthy Elderly Population", *Annals New York Academy of Sciences*, pp. 562–564 (date unknown).

Verhoef, P. et al., "A Common Mutation in the Methylenetetrahydrofolate Reductase Gene and Risk of Coronay Heart Disease: Results Among U.S. Men", *JACC*, vo. 32, No. 2, pp. 353–359 (Aug. 1998).

Verhoef, P. et al., "Homocysteine Metabolism and Risk of Myocardial Infarction: Relation with Vitamins $B_6$, $B_{12}$, and Folate", *Am. J. Epidemiol.*, vol. 143, No. 9, pp. 845–859 (May 1, 1996).

Vermaak, W.J.H. et al., "Vitamin $B_6$ and coronary artery disease. Epidemiological observations and case studies", *Atherosclerosis*, vol. 63, pp. 235–238 (Feb. 1987).

Vidrio, H., "Interaction with Pyridoxal as a Possible Mechanism of Hydralazine Hypotension", *Journal of Cardiovascular Pharmacology*, vol. 15, pp. 150–156 (1990).

Viscontini, V. et al., "Über einige Derivate des Pyridoxals", *Helvetica Chimica Acta*, vol. 34, No. 296, pp. 2438–2439 (1951).

Windebank, A., "Neurotoxicity of Pyridoxine Analogs Is Related to Coenzyme Structure", *Neurochemical Pathology*, vol. 3, pp. 159–167 (1985).

Yamagata, S. et al., "Therapeutic Effects of Pyridoxal Phosphate on Diabetic Neuropathy", *Bitamin*, vol. 35, No. 6, pp. 485–493 (1967). (Abstract provided in English).

Yan, S. et al., "A Role for Pyridoxal Phosphate in the Control of Dephosphorylation of Phosphorylase a", *The Journal of Biological Chemistry*, vol. 264, No. 17, pp. 8263–8269 (1979).

Yarat, A. et al., "Effect of vitamin B6 on lenses of diabetic rats", *Indian Journal of Experimental Biology*, vol. 36, pp. 1269–1272 (Dec. 1998).

Zempleni, J. et al., "The utilization of intravenously infused pyridoxine in humans", *Clinica Chimica Acta*, vol. 229, Nos. 1, 2, pp. 27–36 (Sep. 1994).

PYRIDOXINE AMD PYRIDOXAL ANALOGUES: CARDIOVASCULAR THERAPEUTICS

CROSS-REFERENCE TO RELATED APPLICATION

This application claims the benefit of U.S. Provisional Application Serial No. 60/216,907 filed Jul. 7, 2000, which is hereby incorporated by reference.

FIELD OF THE INVENTION

The present invention relates to pyridoxine and pyridoxal analogue compounds, pharmaceutical compositions containing the pyridoxine and pyridoxal analogue compounds, and methods of treatment using a therapeutically effective amount of the pyridoxine and pyridoxal analogue compounds. The pyridoxine and pyridoxal analogues can be used in the treatment of cardiovascular or related diseases, and symptoms thereof.

BACKGROUND OF THE INVENTION

Pyridoxal-5'-phosphate (PLP), an end product of vitamin $B_6$ metabolism, plays a vital role in mammalian health. Vitamin $B_6$ typically refers to pyridoxine, which is chemically known as 2-methyl-3-hydroxy-4,5-di(hydroxymethyl) pyridine and is represented by formula I:

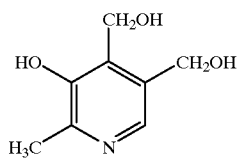

I

Yet two additional compounds, pyridoxal of formula II

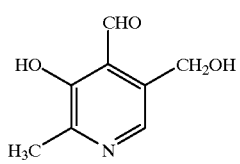

II and pyridoxamine of formula III

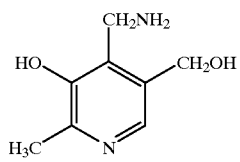

III are also referred to as vitamin $B_6$. All three compounds serve as precursors to pyridoxal-5'-phosphate (PLP), which is chemically known as 3-hydroxy-2-methyl-5-[(phosphonooxy) methyl]-4-pyridine-carboxaldehyde and is represented by formula IV:

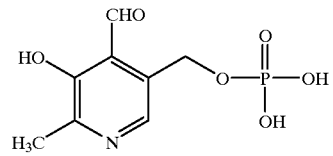

IV

PLP is the biologically active form of vitamin $B_6$ inside cells and in blood plasma. Mammals cannot synthesize PLP de novo and must rely on dietary sources of the precursors pyridoxine, pyridoxal, and pyridoxamine, which are metabolized to PLP. For instance, mammals produce PLP by phosphorylating pyridoxine by action of pyridoxal kinase and then oxidizing the phosphorylated product.

PLP is a regulator of biological processes and a cofactor in more than one hundred enzymatic reactions. It has been shown to be an antagonist of a purinergic receptor, thereby affecting ATP binding; it has been implicated in modulation of platelet aggregation; it is an inhibitor of certain phosphatase enzymes; and it has been implicated in the control of gene transcription. In previous patents (U.S. Pat. Nos. 6,051,587 and 6,043,259) the role of pyridoxal-5'-phosphate, and its precursors pyridoxal and pyridoxine (vitamin $B_6$), in mediating cardiovascular health and in treating cardiovascular related diseases is disclosed. PLP is also a coenzyme in certain enzyme-catalyzed processes, for example, in glycogenolysis at the glycogen phosphorylase level, in the malate asparatate shuttle involving glycolysis and glycogenolysis at the transamination level, and in homocysteine metabolism.

There is a need to identify and administer drugs that can mimic one or more of the known biological actions of vitamin B-6 congeners but that are more potent than the vitamin B-6 congeners in their specific mode of action.

SUMMARY OF THE INVENTION

The present invention provides for pyridoxine and pyridoxal analogues, pharmaceutical compositions containing the pyridoxine and pyridoxal analogues, and methods for treatment based on administration of therapeutically effective amounts of the pyridoxine and pyridoxal analogues. Compounds and compositions of the invention can be used for the treatment of cardiovascular or related diseases and symptoms thereof.

The invention provides pyridoxine and pyridoxal analogues of Formula V:

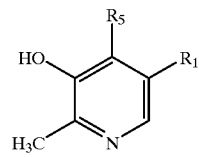

V or a pharmaceutically acceptable acid addition salt addition salt thereof, wherein:

$R_5$ is $CH_2OH$ or $CHO$;
$R_1$ is

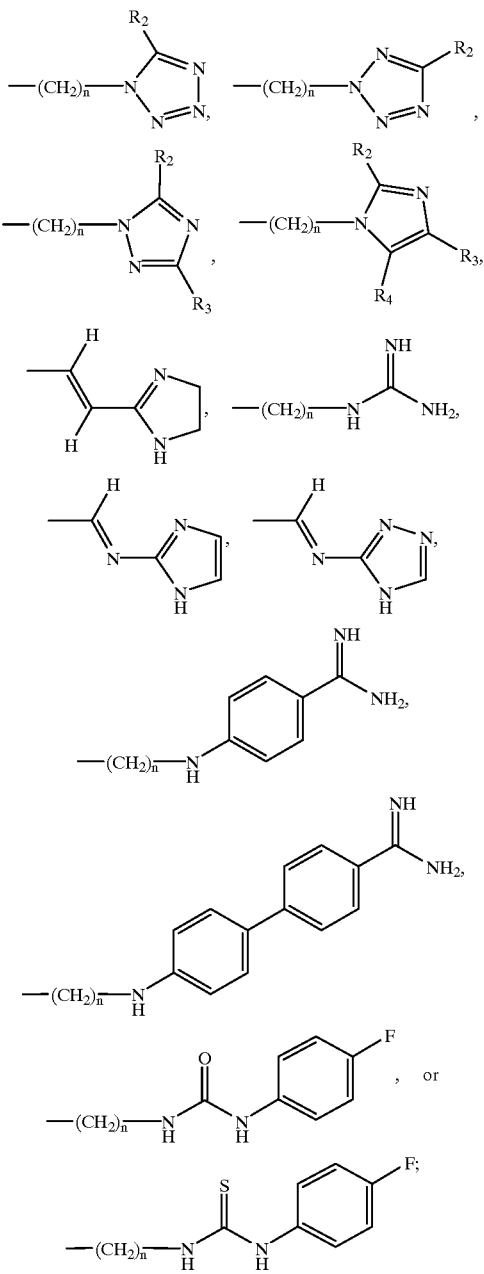

n is an integer of 1 to 5;
$R_2$, $R_3$, and $R_4$ are each independently
  hydrogen;
  alkyl;
  aryl or biaryl,
    wherein the aryl or biaryl can be substituted with a cyano, alkyl, alkoxy, amino, hydroxy, halo, nitro, or alkanoyloxy;
  amino;
  acylamino;
  anilino,
    wherein the aniline ring can be substituted with a cyano, alkyl, alkoxy, amino, hydroxy, halo, nitro, or alkanoyloxy;
  nitro; or
  guanidino.

In another aspect, the invention is directed to a pharmaceutical composition that includes a pharmaceutically acceptable carrier in combination with a therapeutically effective amount of a compound of Formula V or a pharmaceutically acceptable acid addition salt of a compound of Formula V.

In another aspect, the invention is directed to a method of treating cardiovascular or related diseases and symptoms thereof. The method includes administering to a mammal a therapeutically effective amount of a compound of Formula V or a pharmaceutically acceptable acid addition salt of a compound of Formula V in a unit dose form. The method can further include concurrent administration of another therapeutic agent.

DETAILED DESCRIPTION OF THE INVENTION

The invention provides pyridoxal and pyridoxine analogues and pharmaceutical compositions containing these pyridoxine and pyridoxal analogues. The pyridoxine and pyridoxal analogues can be used in the treatment of cardiovascular or related diseases and symptoms thereof.

Cardiovascular or related diseases include, for example, cerebral ischemia, cerebral hemorrhage, ischemic stroke, hemorrhagic stroke, hypertension, myocardial infarction, ischemia reperfusion injury, myocardial ischemia, congestive heart failure, blood coagulation disorders, cardiac hypertrophy, and platelet aggregation. Cardiovascular or related diseases also includes diseases that arises from thrombotic and prothrombotic states in which the coagulation cascade is activated such as, for example, deep vein thrombosis, disseminated intravascular coagulopathy, and pulmonary embolism.

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure can ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic pressure, diastolic blood pressure, or both. Hypertension places increased tension on the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ affected is the heart, this condition is known as myocardial ischemia, and myocardial ischemia initially leads to abnormal electrical activity. This can generate an arrhythmia. When myocardial ischemia is of sufficient severity and duration, cell injury can progress to cell death—i.e., myocardial infarction—and subsequently to heart failure, hypertrophy, or congestive heart failure.

Ischemic reperfusion of the organ occurs when blood flow resumes to an organ after temporary cessation. For example, reperfusion of an ischemic myocardium can counter the effects of coronary occlusion, a condition that leads to myocardial ischemia. Ischemic reperfusion to the myocardium can lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Pyridoxal and Pyridoxine Analogue Compounds

The invention provides pyridoxal and pyridoxine analogue compounds of Formula V:

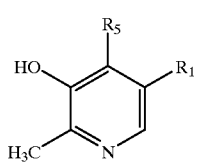

or pharmaceutically acceptable acid addition salts thereof, wherein:

$R_5$ is $CH_2OH$ or $CHO$;

$R_1$ is

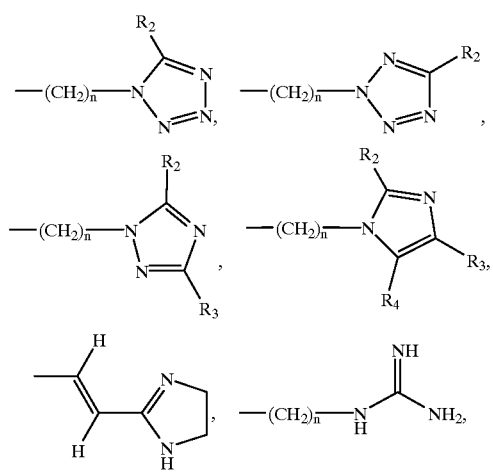

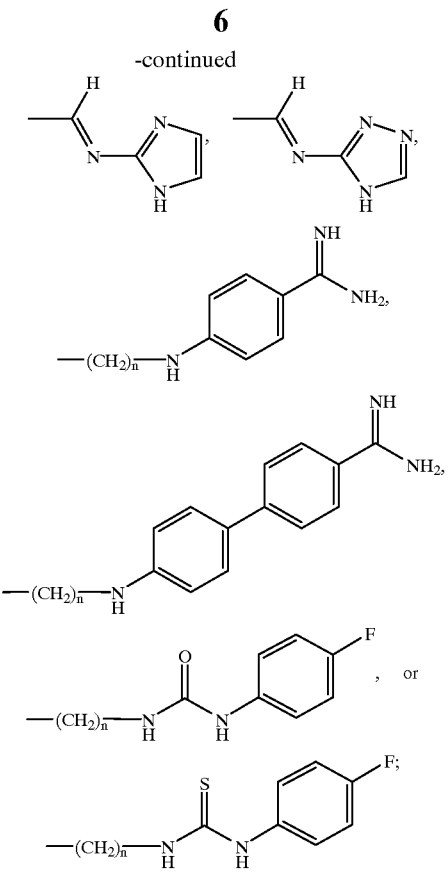

n is an integer of 1 to 5;

$R_2$, $R_3$, and $R_4$ are each independently
    hydrogen;
    alkyl;
    aryl or biaryl;
        wherein the aryl or biaryl can be substituted with a cyano, alkyl, alkoxy, amino, hydroxy, halo, nitro, or alkanoyloxy;
    amino;
    acylamino;
    anilino,
        wherein the aniline ring can be substituted with a cyano, alkyl, alkoxy, amino, hydroxy, halo, nitro, or alkanoyloxy;
    nitro; or
    guanidino.

As used herein, the term "alkyl" refers to a straight or branched saturated aliphatic hydrocarbon chain having 1 to 8 carbon atoms, such as, for example, methyl, ethyl, propyl, isopropyl (1-methylethyl), butyl, tert-butyl (1,1-dimethylethyl), and the like. The alkyl chain can be interrupted by a heteroatom, such as, for example, a nitrogen, sulfur, or oxygen atom, forming an alkylaminoalkyl, alkylthioalkyl, or alkoxyalkyl. Examples of alkyl chain interrupted by a heteroatoms include methylaminoethyl, ethylthiopropyl, methoxymethyl, and the like. The alkyl can be substituted at the terminal carbon by groups such as hydroxy, alkoxy, alkanoyloxy, alkoxycarbonyl, or carboxy.

The term "alkoxy" refers to an alkyl group joined to an oxygen atom. In some embodiments, the alkoxy has 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

As used herein, the term "alkanoyloxy" refers to a group of formula

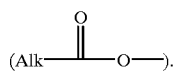

Examples of an alkanoyloxy include methanoyloxy, ethanoyloxy, propanoyloxy, and the like.

The term "halo" refers to a bromo, chloro, or fluoro group. In some embodiments, the halo is fluoro.

Pharmaceutically acceptable acid addition salts of the compounds of Formula V include salts derived from non-toxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicar-boxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., *J. Pharmaceutical Science*, 66: 1–19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

In one embodiment of Formula V, $R_1$ is

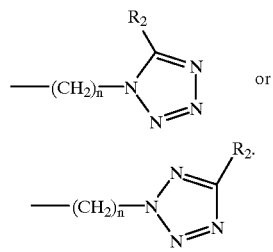

Preferably, $R_2$ is hydrogen, alkyl, or amino.

In another embodiment of Formula V, $R_1$ is

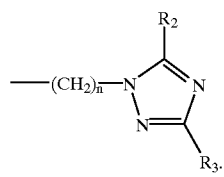

Preferably, $R_2$ and $R_3$ are each independently hydrogen, alkyl, amino, or nitro.

In another embodiment of Formula V, $R_1$ is

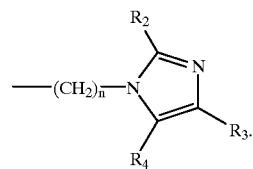

Preferably, $R_2$, $R_3$, and $R_4$ are independently hydrogen, alkyl, or amino. In a particularly preferred embodiment, $R_2$ is hydrogen, $R_3$ is methyl, and $R_4$ is hydrogen.

In another embodiment of Formula V, $R_1$ is

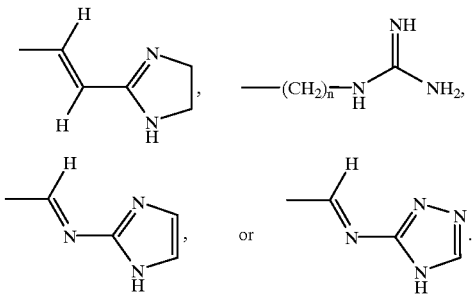

In still another embodiment of Formula V, $R_1$ is

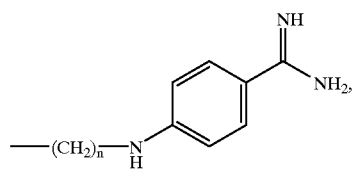

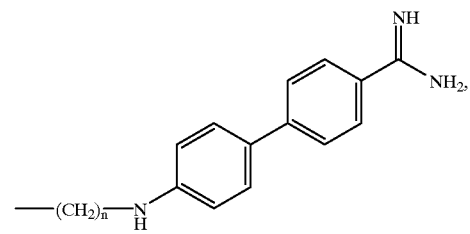

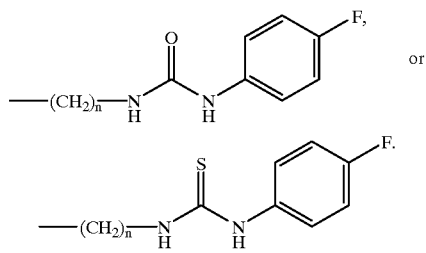

particularly preferred embodiment, $R_1$ is

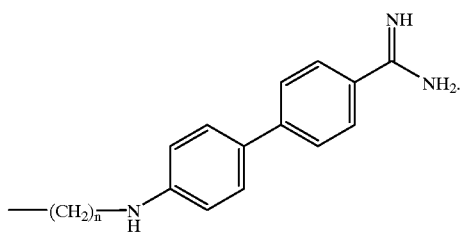

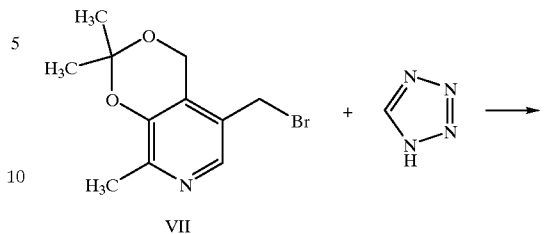

Scheme 1

Methods of Preparing Pyridoxal and Pyridoxine Analogue Compounds

Another aspect of the invention provides a method for preparing the pyridoxine and pyridoxal analogues. The compounds of the invention can be prepared from a compound of Formula VI, VII, VIII, IX, or X:

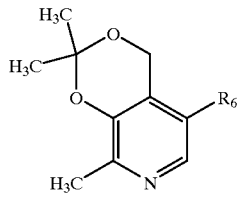

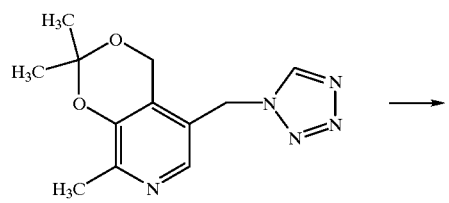

XI

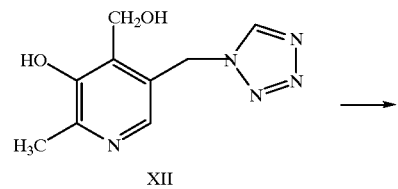

XII

VI $R_6=(CH_2)_pOH$ where p=1 to 5

VII $R_6=(CH_2)_qBr$ where q=1 to 5

VIII $R_6=(CH_2)_rCHO$ where r=0 to 4

IX $R_6=(CH_2)_sN_3$ where s=1 to 5

X $R_6=(CH_2)_tNH_2$ where t=1 to 5

A compound of Formula VI, VII, VIII, IX, or X can be used to form the compounds of Formula V through a series of chemical reactions to produce pyridoxine analogues. The pyridoxine analogues can be subsequently oxidized to produce the corresponding pyridoxal analogues.

In some embodiments of the invention, the pyridoxine and pyridoxal analogues are formed by reacting a bromide compound of Formula VII with a substituted or unsubstituted tetrazole, a substituted or unsubstituted triazole, or a substituted or unsubstituted imidazole. The tetrazole, triazole, or imidazole can be substituted with an aryl, biaryl, amino, acylamino, anilino, or guanidine. An aryl or biaryl can be further substituted with a cyano, alkyl, alkoxy, amino, hydroxy, halo, nitro, or alkanoyloxy group. An aniline can be further substituted with a cyano, alkyl, alkoxy, amino, hydroxy, halo, nitro, or alkanoyloxy group.

For example, as shown in Scheme 1, a bromide compound of Formula VII (q=1) can be reacted with 1H-tetrazole to produce derivative XI. The derivative XI is then treated with acetic acid to produce 5-tetrazolepyridoxine XII. Oxidation of 5-tetrazolepyridoxine XII in the presence of a catalyst such as manganese dioxide can be use to produce the corresponding pyridoxal XIII.

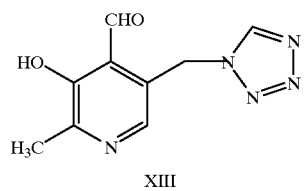

XIII

In other embodiments of the invention, an aldehyde of Formula VIII is formed by reacting an alcohol of Formula VI with a suitable oxidizing agent such as manganese doxide. The pyridoxine and pyridoxal analogues of Formula V are formed by reacting an aldehyde of Formula VIII with a substituted or unsubstituted triazole, a substituted or unsubstituted imidazole, or a substituted or unsubstituted alinine. The triazole, or imidazole can be substituted with an aryl, biaryl, amino, acylamino, anilino, or guanidine. An aryl or biaryl can be further substituted with a cyano, alkyl, alkoxy, amino, hydroxy, halo, nitro, or alkanoyloxy group. An aniline can be further substituted with a cyano, alkyl, alkoxy, amino, hydroxy, halo, nitro, or alkanoyloxy group.

For example, an aldehyde of Formula VIII (r=0) can react with 2-methylimidazoline to form the protected imidazoline derivative XXVIII according to Scheme 2. The protected imidazoline derivative XXVII can be hydrolyzed to the imidazoline XXIX.

Scheme 2

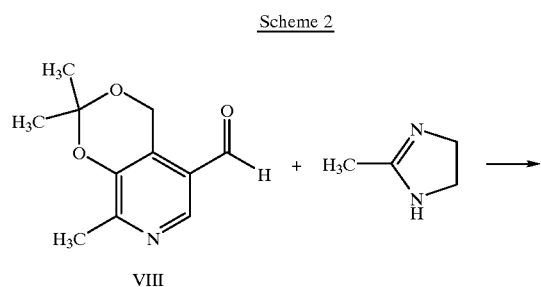

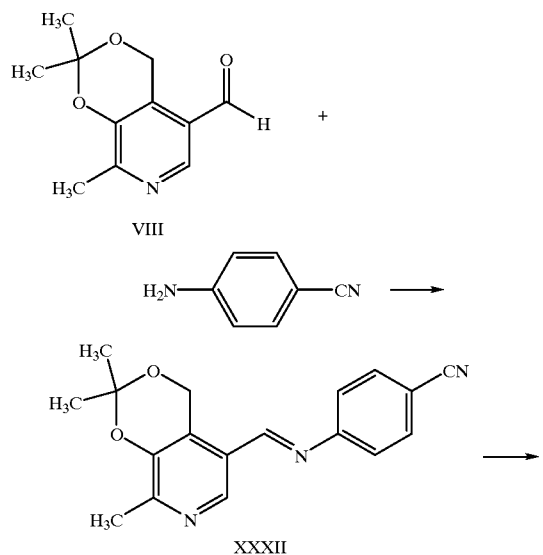

In another example, a compound of the invention can be prepared by reacting an aldehyde of Formula VIII (r=0) with 4-cyano aniline as shown in Scheme 3 to form a Schiff base. The Schiff base XXXII is reacted with a strong reducing agent such as, for example, sodium borohydride. The resulting amine XXXIII can react with ethanol in the presence of dry hydrogen chloride gas to form a compound of Formula XXXIV. The compound of Formula XXXIV can be treated with 2 M NH$_3$ in MeOH in a pressurized vessel to form the compound of Formula XXXV.

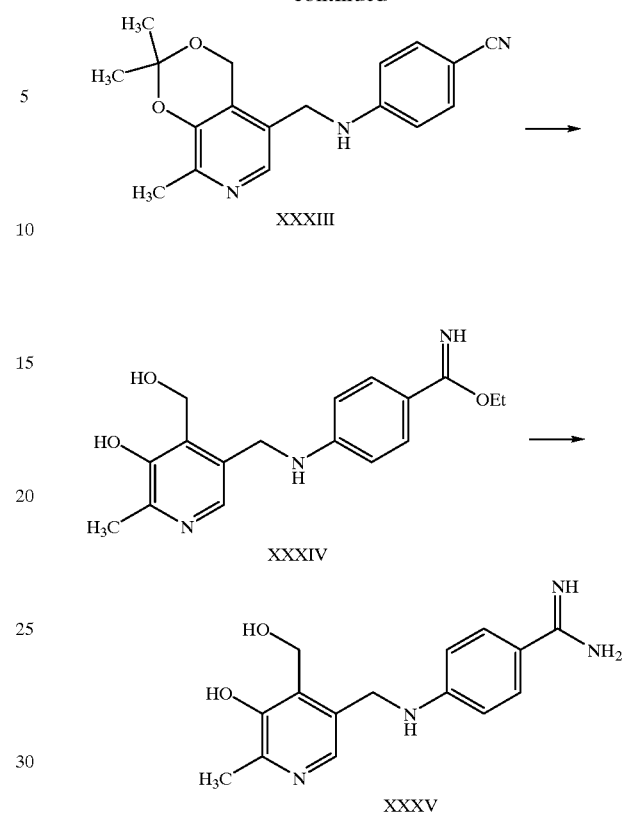

In another embodiment of preparing the compounds of Formula V, an amine of Formula X can react with a substituted guanidine.

For example, as shown in Scheme 4, an amine compound of Formula X (s=1) can react with a protected guanidine compound to give the guanidine derivative XXIII. The protection groups can be removed with trifluoroacetic acid to form a compound of Formula XXV.

Scheme 4

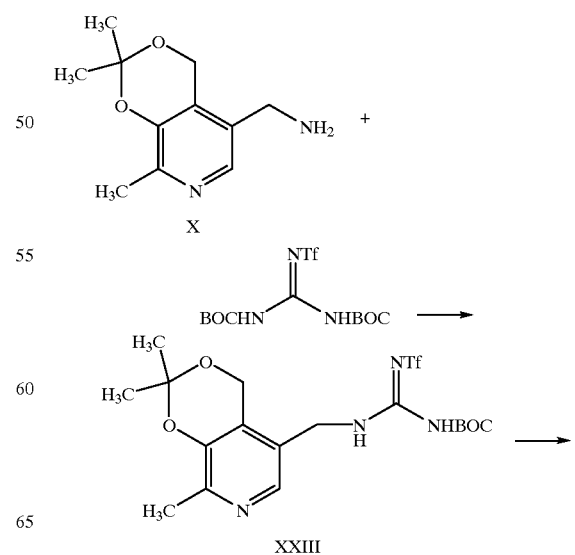

-continued

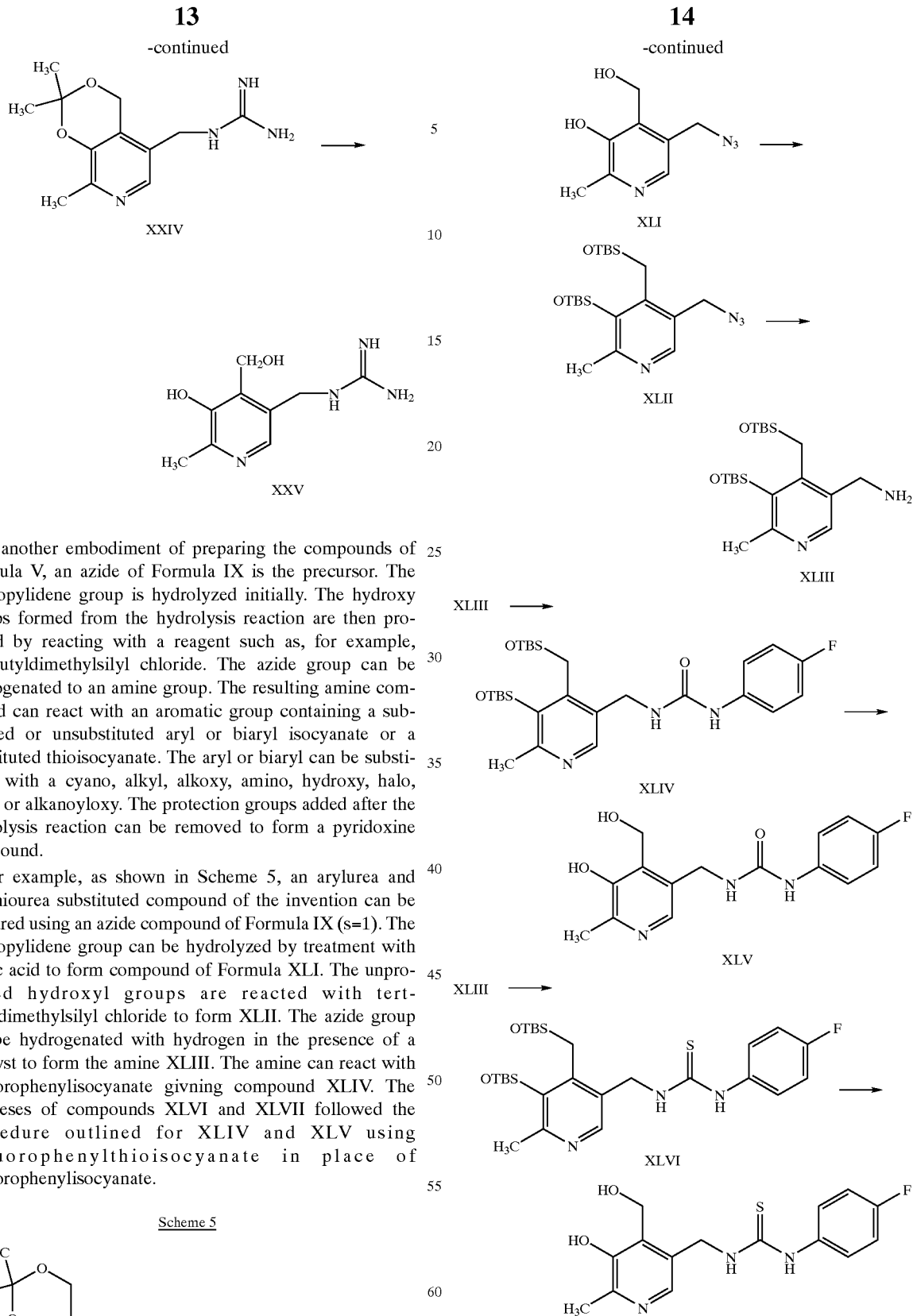

In another embodiment of preparing the compounds of Formula V, an azide of Formula IX is the precursor. The isopropylidene group is hydrolyzed initially. The hydroxy groups formed from the hydrolysis reaction are then protected by reacting with a reagent such as, for example, tert-butyldimethylsilyl chloride. The azide group can be hydrogenated to an amine group. The resulting amine compound can react with an aromatic group containing a substituted or unsubstituted aryl or biaryl isocyanate or a substituted thioisocyanate. The aryl or biaryl can be substituted with a cyano, alkyl, alkoxy, amino, hydroxy, halo, nitro, or alkanoyloxy. The protection groups added after the hydrolysis reaction can be removed to form a pyridoxine compound.

For example, as shown in Scheme 5, an arylurea and arylthiourea substituted compound of the invention can be prepared using an azide compound of Formula IX (s=1). The isopropylidene group can be hydrolyzed by treatment with acetic acid to form compound of Formula XLI. The unprotected hydroxyl groups are reacted with tert-butyldimethylsilyl chloride to form XLII. The azide group can be hydrogenated with hydrogen in the presence of a catalyst to form the amine XLIII. The amine can react with 4-fluorophenylisocyanate givning compound XLIV. The syntheses of compounds XLVI and XLVII followed the procedure outlined for XLIV and XLV using 4-fluorophenylthioisocyanate in place of 4-fluorophenylisocyanate.

Scheme 5

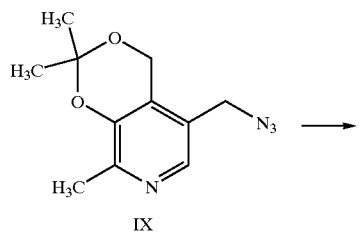

The products of the reactions described herein are isolated by conventional means such as extraction, distillation, chromatography, and the like.

One skilled in the art can recognize other variations in the reaction sequences and in the appropriate reaction conditions from the analogous reactions shown or otherwise known that may be appropriately used in the above-described processes to make the compounds of Formula V herein.

Pharmaceutical Compositions

Although it is possible for a pyridoxine and pyridoxal analogue compound of the invention to be administered alone in a unit dosage form, the compounds are typically administered in admixture as a pharmaceutical composition to provide a unit dosage form. The invention provides pharmaceutical compositions containing at least one pyridoxine or pyridoxal analogues compound of Formula V. A pharmaceutical composition comprises a pharmaceutically acceptable carrier in combination with a compound of Formula V or a pharmaceutically acceptable acid addition salt of a compound of Formula V.

A pharmaceutically acceptable carrier includes, but is not limited to, physiological saline, ringers, phosphate-buffered saline, and other carriers known in the art. Pharmaceutical compositions can also include additives such as, for example, stabilizers, antioxidants, colorants, excipients, binders, thickeners, dispersing agents, readsorption enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier in combination with a therapeutic compound of Formula V or a pharmaceutically acceptable acid addition salt of a compound of Formula V are known to those of skill in the art. All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage forms.

For oral administration as a suspension, the compositions can be prepared according to techniques well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Method of Treatment Using Pyridoxal and Pyridoxine Analogue Compounds

In another aspect of the invention, methods are provided for the treatment of cardiovascular or related diseases and symptoms thereof.

As used herein, the terms "treatment" and "treating" as used herein include preventing, inhibiting, alleviating, and healing vitamin $B_6$ cardiovascular or related diseases or symptoms thereof. Treatment can be carried out by administering a therapeutically effective amount of a compound of the invention. A "therapeutically effective amount" as used herein includes a prophylactic amount, for example, an amount effective for preventing or protecting against the above mentioned diseases or symptoms thereof; or an amount effective for alleviating or healing the above mentioned diseases or symptoms thereof.

A physician or veterinarian of ordinary skill readily determines a mammalian subject who is exhibiting symptoms of any one or more of the diseases described above. Regardless of the route of administration selected, a compound of Formula V or a pharmaceutically acceptable acid addition salt of a compound of Formula V can be formulated into pharmaceutically acceptable unit dosage forms by conventional methods known in the pharmaceutical art. An effective but nontoxic quantity of the compound is employed in treatment. The compounds can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and by other administrative methods known in the art.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating cardiovascular or related diseases or symptoms thereof, is in a range of about 0.1–100 mg/kg of a patient's body weight, more preferably in the range of about 0.5–50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose usually does not exceed 25 mg/kg of a patient's body weight.

A therapeutically effective amount of a compound of Formula V or a pharmaceutically acceptable addition salt of a compound of Formula V for treating the above-identified diseases or symptoms thereof can be administered prior to, concurrently with, or after the onset of the disease or symptom. A compound of the invention can be administered concurrently. "Concurrent administration" and "concurrently administering" as used herein includes administering a compound of the invention and another therapeutic agent in admixture, such as, for example, in a pharmaceutical composition or in solution, or separately, such as, for example, separate pharmaceutical compositions or solutions administered consecutively, simultaneously, or at different times but not so distant in time such that the compound of the invention and the other therapeutic agent cannot interact and a lower dosage amount of the active ingredient cannot be administered.

In one embodiment of the invention, a method is provided for treating cardiovascular or related diseases comprising administering to a mammal a therapeutically effective amount of a compound of Formula V or a pharmaceutically acceptable addition salt of a compound of Formula V in a unit dosage form. The cardiovascular or related diseases that can be treated include hypertrophy, hypertension, congestive heart failure, heart failure subsequent to myocardial infarction, myocardial ischemia, cerebral ischemia, ischemia reperfusion injury, arrhythmia, myocardial infarction, blood coagulation, or platelet aggregation. Preferably, the cardiovascular disease treated is hypertrophy, congestive heart failure, arrhythmia, or ischemia reperfusion injury.

The compound of the invention can also be administered to treat cardiovascular diseases and other diseases that arise from thrombotic and prothrombotic states in which the coagulation cascade is activated, such as, for example, deep vein thrombosis, disseminated intravascular coagulopathy, Kasabach-Merritt syndrome, pulmonary embolism, myocardial infarction, stroke, thromboembolic complications of surgery, and peripheral arterial occlusion. A compound of the invention may also be useful in the treatment of adult respiratory distress syndrome, septic shock, septicemia, or inflammatory responses, such as edema and acute or chronic atherosclerosis, because thrombin has been shown to activate a large number of cells outside of the coagulation process, such as, for example, neutrophils, fibroblasts, endothelial cells, and smooth muscle cells.

The method for treating cardiovascular or related diseases can further comprise concurrent administration of other therapeutic agents already known to be suitable for treating the above-identified diseases. For example, methods of the invention include concurrently administering a compound of Formula V or a pharmaceutically acceptable acid addition salt of a compound of Formula V in combination with a therapeutic cardiovascular compound to treat hypertrophy, hypertension, congestive heart failure, heart failure subsequent to myocardial infarction, myocardial ischemia, ischemia reperfusion injury, arrhythmia, or myocardial infarction. Preferably, the cardiovascular disease treated is hypertrophy, congestive heart failure, arrhythmia, or ischemia reperfusion injury.

Other therapeutic cardiovascular compounds that can be concurrently administered with a compound or composition of the invention include an angiotensin converting enzyme inhibitor, an angiotensin II receptor antagonist, a calcium channel blocker, an antithrombolytic agent, a β-adrenergic receptor antagonist, a vasodilator, a diuretic, an α-adrenergic receptor antagonist, an antioxidant, and a mixture thereof. In one embodiment, a compound of the invention is administered concurrently with PPADS (pyridoxal phosphate-6-azophenyl-2',4'-disulphonic acid), also a therapeutic cardiovascular compound, or concurrently with PPADS and another known therapeutic cardiovascular compound as already described.

Preferably the other therapeutic cardiovascular compound, which is concurrently administered with a compound of Formula V or a pharmaceutically acceptable acid addition salt of a compound of Formula V, is an angiotensin converting enzyme inhibitor, an angiotensin II receptor antagonist, a diuretic, an α-adrenergic receptor antagonist, or a calcium channel blocker.

Known angiotensin converting enzyme inhibitors include, for example, captopril, enalapril, lisinopril, benazapril, fosinopril, quinapril, ramipril, spirapril, imidapril, and moexipril.

Examples of known angiotensin II receptor antagonists include both angiotensin I receptor subtype antagonists and angiotensin II receptor subtype antagonists. Suitable antiotensin II receptor antagonists include losartan and valsartan.

Suitable calcium channel blockers include, for example, verapamil, diltiazem, nicardipine, nifedipine, amlodipine, felodipine, nimodipine, and bepridil.

Examples of known β-adrenergic receptor antagonists include atenolol, propranolol, timolol, and metoprolol.

Suitable vasodilators include, for example, hydralazine, nitroglycerin, and isosorbide dinitrate.

Suitable diuretics include, for example, furosemide, diuril, amiloride, and hydrodiuril.

Suitable α-adrenergic receptor antagonists include, for example, prazosin, doxazocin, and labetalol.

Suitable antioxidants include vitamin E, vitamin C, and isoflavones.

These other therapeutic cardiovascular compounds are generally used to treat cardiovascular or related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of a compound of Formula V or a pharmaceutically acceptable acid addition salt of a compound of Formula V concurrently with another therapeutic agent. Other suitable therapeutic agents include, for example, a angiotensin converting enzyme inhibitor, an angiotensin II receptor antagonist, a calcium channel blocker, an antithrombolytic agent, a β-adrenergic receptor antagonist, a diuretic, an I-adrenergic receptor antagonist, or a mixture thereof.

As another example, congestive heart failure can be treated by the administration of a compound of Formula V or a pharmaceutically acceptable acid addition salt of a compound of Formula V concurrently with another therapeutic agent. Other suitable therapeutic agents include, for example, a angiotensin converting enzyme inhibitor, an angiotensin II receptor antagonist, a calcium channel blocker, a vasodilator, a diuretic, or a mixture thereof.

Myocardial infarction can be treated by the administration of a compound of Formula V or a pharmaceutically acceptable acid addition salt of a compound of Formula V concurrently with another therapeutic agent. Other suitable therapeutic agents include, for example, a angiotensin converting enzyme inhibitor, a calcium channel blocker, an antithrombolytic agent, a β-adrenergic receptor antagonist, a diuretic, an—adrenergic receptor antagonist, or a mixture thereof.

Hypertension can be treated by the administration of a compound of Formula V or a pharmaceutically acceptable acid addition salt of a compound of Formula V concurrently with another therapeutic agent. Other suitable therapeutic agents include, for example, an angiotensin converting enzyme inhibitor, a calcium channel blocker, a β-adrenergic receptor antagonist, a vasodilator, a diuretic, an α-adrenergic receptor antagonist, or a mixture thereof.

Arrhythmia can be treated by the administration of a compound of Formula V or a pharmaceutically acceptable acid addition salt of a compound of Formula V concurrently with another therapeutic agent. Other suitable therapeutic agents include, for example, a calcium channel blocker, a β-adrenergic receptor antagonist, or a mixture thereof.

Blood clots in the arteries can be reduced or removed by the administration of a compound of Formula V or a pharmaceutically acceptable acid addition salt of a compound of Formula V concurrently with an antithrombolytic agent. Antithrombolytic agents known in the art include antiplatelet agents, aspirin, and heparin.

Hypertrophy can be treated by the administration of a compound of Formula V or a pharmaceutically acceptable acid addition salt of a compound of Formula V concurrently with another therapeutic agent. Other suitable therapeutic agents include, for example, an angiotensin converting enzyme inhibitor, an angiotensin II receptor antagonist, a calcium channel blocker, or a mixture thereof.

Ischemia reperfusion injury can be treated by the administration of a compound of Formula V or a pharmaceutically acceptable acid addition salt of a compound of Formula V concurrently with another therapeutic agent. Other suitable therapeutic agents include, for example, an angiotensin converting enzyme inhibitor, an angiotensin II receptor antagonist, a calcium channel blocker, or a mixture thereof.

This invention is further characterized by the following examples. These examples are not meant to limit the scope of the invention but are provided for exemplary purposes to more fully describe the invention. Variation within the scope of the invention will be apparent to those skilled in the art.

EXAMPLES

Preparation of Starting Materials

Bromide VII (q=1) was prepared by a literature procedure; Imperalli et al, *J. Org. Chem.*, 60, 1891–1894 (1995). Alcohol VI (p=1) was prepared by bubbling HCl gas into a solution of pyridoxine hydrochloride (50 g, 0.24 mol) in acetone (500 mL) at 0–5° C. (ice bath) until the solution became clear. Diethyl ether (ca. 1 L) was added to induce precipitation of the hydrochloride salt which was filtered off. The salt was dissolved in a mixture of methylene chloride (ca. 1 L) and saturated aqueous NaHCO$_3$ (ca. 500 mL). The layers were separated and the organic layer washed with saturated aqueous NaHCO$_3$. The combined organic layers were dried (MgSO$_4$), and evaporated to give 40.5 g (80%) of a colourless solid.

Alcohol VI (p=1) was dissolved in dichloromethane and cooled to 0° C. Small of amounts of triphenylphosphine and N-bromosuccinimide were added alternately over a period of about five minute. The reaction mixture was stirred for about 20 minutes and then concentrated in vacuo. The crude product, bromide VII (q=1) was purified by flash chromatography using a 2:1 mixture of ether and hexanes as the eluent. The product was used immediately.

Aldehyde VIII (r=0) was identified by comparison to data in the literature; Kortynk et al., *J. Org. Chem.*, 29, 574–579 (1964). MnO$_2$ (Aldrich 21,764-6) (49.9 g, 85%, 487 mmol) was added to a solution of alcohol VI (p=1) (25 g, 119.6 mmol) in toluene (900 ml). The resulting mixture was stirred at 40° C. for 24 hours then filtered through Celite. The mother liquor was evaporated to give a light yellow solid. The solid was recrystallized from hexane:ethyl ether (1:1) to give a light yellow solid. The solid was filtered and washed with hexane:ethyl ether (1:1) to give the pure aldehyde VIII (17.51 g, 71%).

Azide IX (s=1) and amine X (t=1) were prepared from bromide VII (q=1). Bromide VII (q=1) (1.08 g. 4.0 mmol) in anhydrous DMF (20 ml) was treated with sodium azide (260 mg, 4.0 mmol) at room temperature. After one hour stirring at room temperature, the solution was extracted with diethyl ether (5×20 mL). The combined extracts were washed with water (10 mL) and brine (10 mL) followed by drying (MgSO$_4$). The solvent was evaporated and the crude product was purified by chromatography on silica gel using ethyl ether: hexanes (2:1) as eluent to give the azide IX (s=1) as a colourless liquid (552 mg, 60%). $^1$H NMR (CDCl$_3$, TMS) δ1.57 (s, 6H), 2.42 (s, 3H), 4.23 (s, 2H), 4.86 (s, 2H), 7.96 (s, 1H).

The purified azide IX (s=1) (100 mg, 0.4 mmol) was dissolved in 95% ethanol and hydrogenated at 1 atm in presence of Lindlar catalyst (50 mg) for one hour. The catalyst was removed by filtration (Celite), and the solvent removed to give the crude amine X (t=1). Purification by chromatography on silica gel using CH$_2$Cl$_2$:MeOH (5:1) as eluent gave the product (80 mg, 82%) $^1$HNMR (CD$_2$Cl$_2$) 1.53 (s, 6H), 2.34 (s, 3H), 3.72 (s, 2H), 4.91 (s, 2H), 5.31 (s, 2H), 7.93 (s, 1H).

All other reagents used in the following examples can be purchased from Aldrich Chemical Company (Milwaukee, Wis. or Allentown, Pa.).

Example 1

Synthesis of Tetrazole Substituted Pyridoxine Analogue of Formula XII

Scheme 1

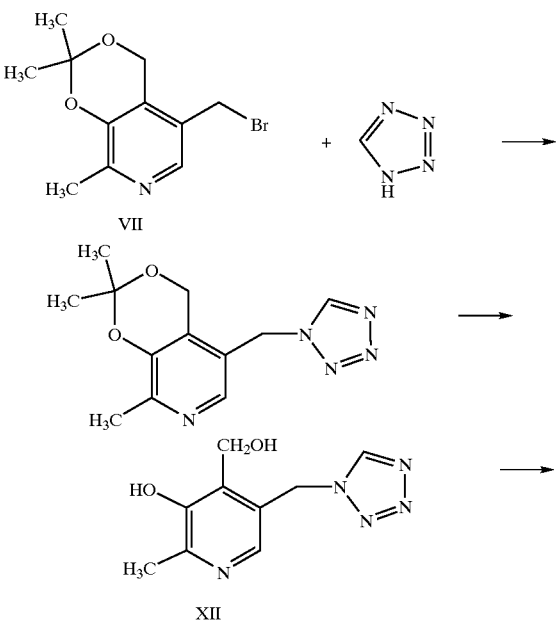

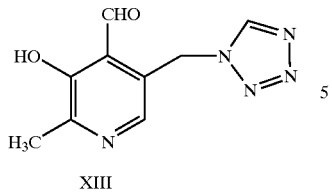

XIII

A mixture of tetrazole (94.2 mg, 1.29 mmol) and pulverized anhydrous potassium carbonate (1.5 g) in anhydrous acetonitrile (10 mL) was stirred at 0° C. for 15 minutes. The bromide VII (q=1) (350 mg, 1.29 mmol) in anhydrous acetonitrile (3 mL) was then added to the reaction mixture maintaining the reaction temperature for the next 30 minutes. After the completion of the reaction, routine work-up gave the crude product. Purification of the crude mixture on silica gel column gave the desired product XI in appreciable yields.

$^1$H nmr (CDCl$_3$, TMS): δ1:52 (6H, s), 2.44 (3H, s), 4.77 (2H, s), 5.47 (2H, s), 8.07 (1H, s), 8.55 (1H, s, -tetrazole-H).

The purified derivative XI (100 mg, 0.4 mmol) was then taken in 80% aqueous acetic acid (10 mL) and heated at 60° C. for 1 hour. Purification by chromatography on silica gel gave the 5-tetrazolepyridoxine XII in good yields.

$^1$H nmr (CD$_3$OD, TMS): δ2.42 (3H, s), 4.96 (2H, s), 5.97 (2H, s), 7.92 (1H, s), 8.69 (1H, s, terazole H).

Example 2

Synthesis of Tetrazole Substituted Pyridoxal Analogue of Formula XIII

The 5-tetrazole pyridoxine XII (100 mg, 0.42 mmol) was dissolved in anhydrous toluene (10 mL). To the solution was added activated manganese dioxide (243 mg, 2.76 mmol), and the reaction mixture heated at 40° C. for 2 hours to ensure complete oxidation. Filtration of the catalyst, followed by evaporation of the solvent gave the crude residue which was easily purified by chromatography on silica gel to give the desired aldehyde XIII in 70% yield.

$^1$H nmr (CD$_2$Cl$_2$, TMS): δ2.82 (3H, s), 6.00 (1H, s), 6.15 (1H, s), 8.11 (1H, s), 8.57 (1H, s, tetrazole-H), 10.77 (1H, s, aldeydic-H).

Example 3

Synthesis of Tetrazole Substituted Pyridoxine Analogue of Formula XV

Scheme 6

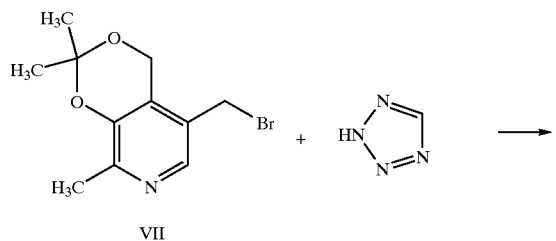

VII

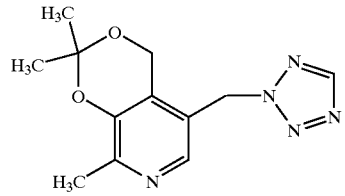

XIV

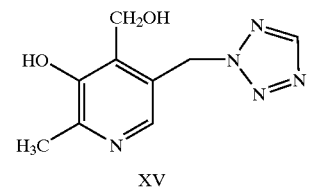

XV

A mixture of tetrazole (94.2 mg, 1.29 mmol) and pulverized anhydrous potassium carbonate (1.5 g) in anhydrous acetonitrile (10 mL) was stirred at 0° C. for 15 minutes. The bromide VII (q=1) (350 mg, 1.29 mmol) in anhydrous acetonitrile (3 mL) was then added to the reaction mixture which was maintained at 0° C. for the next 30 minutes. Routine work-up gave the crude product. Purification of the crude mixture by chromatography on silica gel gave the desired product XIV in appreciable yields.

$^1$H nmr (CDCl$_3$, TMS): δ1:53 (6H, s), 2.42 (3H, s), 4.91 (2H, s), 5.66 (2H, s), 8.14 (1H, s), 8.50 (1H, s,-tetrazole-H).

The purified derivative XIV (100 mg, 0.4 mmol) was dissolved in 80% aqueous acetic acid (10 mL) and heated at 60° C. for 1 hour. Purification by chromatography on silica gel column gave the 5-tetrazole pyridoxine XV in good yields.

$^1$H nmr (CD$_3$OD, TMS): δ2.43 (3H, s), 4.89 (2H, s), 5.77 (2H, s), 7.91 (1H, s), 9.17 (1H, s, terazole H).

Example 4

Synthesis of Tetrazole Substituted Pyridoxine Analogue of Formula XVII

Scheme 7

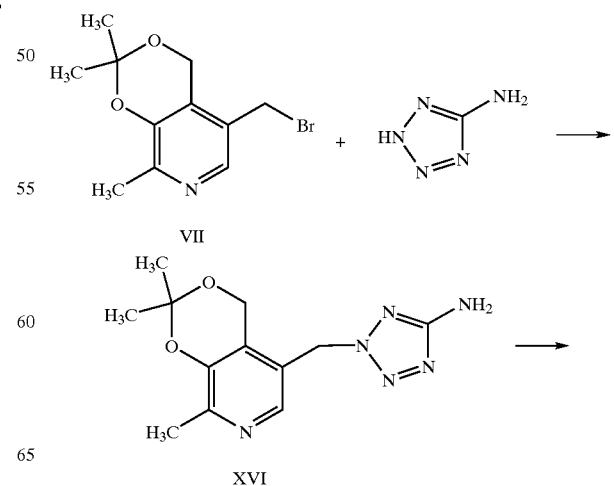

VII

XVI

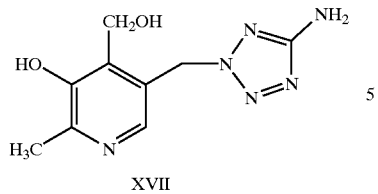

XVII

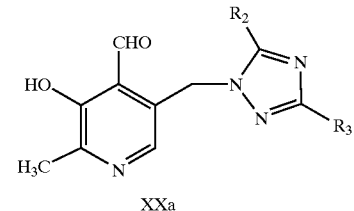

XXa a) $R_2 = R_3 = H$  b) $R_2 = H, R_3 = NH_2$  c) $R_2 = NH_2, R_3 = H$

A mixture of aminotetrazole (110.2 mg, 1.30 mmol) and pulverized anhydrous potassium carbonate (1.5 g) in anhydrous acetonitrile (10 mL) was stirred at 0° C. for 15 minutes. The bromide VII (q=1) (360 mg, 1.30 mmol) in anhydrous acetonitrile (3 mL) was added to the reaction mixture which was maintained at 0° C. for the next 30 minutes. Routine work-up gave the crude product. Purification of the crude mixture by chromatography on a silica gel column gave the desired product XVI in appreciable yields.

$^1$H nmr (CD$_3$OD, TMS): δ1:52 (6H, s), 2.36 (3H, s), 4.96 (2H, s), 5.56 (2H, s), 7.96 (1H, s).

The purified derivative XVI (100 mg, 0.37 mmol) was dissolved in 80% aqueous acetic acid (10 mL) and heated at 60° C. for 1 hour. Purification by chromatography on silica gel gave the 5-tetrazole pyridoxine XVII in good yields.

$^1$H nmr (CD$_3$OD, TMS): δ2.42 (3H,s), 4.94 (2H, s), 5.66 (2H, s), 7.91 (1H, s), 7.87 (1H, s).

Example 5

Synthesis of Triazole Substituted Pyridoxine Analogue of Formula XIXa

Scheme 8

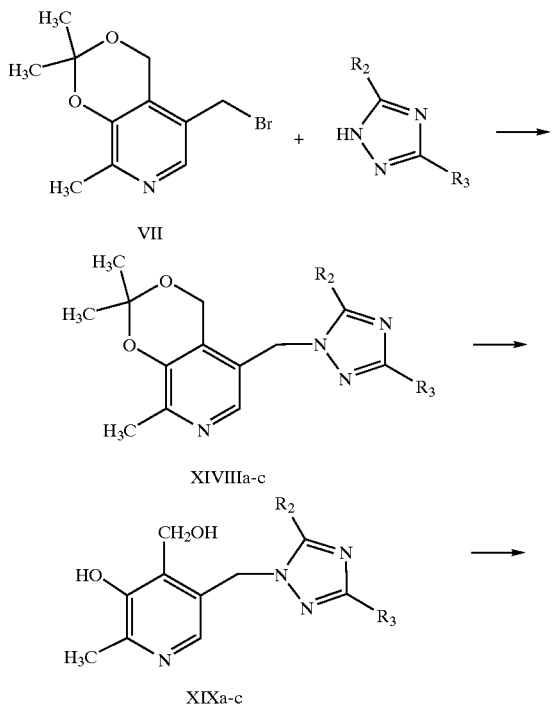

A mixture of triazole (136 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on a silica gel column gave the desired product XVIIIa in appreciable yield.

$^1$H nmr (CDCl$_3$, TMS): δ1:53 (6H, s), 2.42 (3H, s), 4.80 (2H, s), 5.24 (2H, s), 7.94 (1H,s,-triazole-H), 7.99 (1H, s, -triazole-H), 8.15 (1H, s).

The purified derivative XVIIIa (100 mg, 0.35 mmol) was dissolved in 80% aqueous acetic acid (10 mL) and heated at 60° C. Purification by chromatography on silica gel column gave the 5-triazole pyridoxine XIXa in good yield.

$^1$H nmr (CD$_3$OD, TMS): δ2.42 (3H, s), 4.91 (2H, s), 5.50 (2H, s), 7.82 (1H, s, -triazole-H), 7.97 (1H, s, -triazole-H), 8.52 (1H, s).

Example 6

Synthesis of Triazole Substituted Pyridoxal Analogue of Formula XXa

Following Scheme 8, 5-triazole pyridoxine XIXa (100 mg, 0.42 mmol) was dissolved in anhydrous toluene (10 mL). To the solution was added activated manganese dioxide (243 mg, 2.76 mmol), and the reaction mixture heated at 40° C. for 2 hours to ensure complete oxidation. Filtration of the catalyst, followed by evaporation of the solvent gave a crude residue that was easily purified by chromatography on silica gel to give the desired aldehyde XXa in 70% yield.

$^1$H nmr (CD$_3$OD, TMS): δ2.70 (3H, s), 6.00 (2H, s), 6.28 (2H, s), 8,41 (1H, s, -triazole-H), 8.85 (1H, s, -triazole-H), 9.85 (1H, s).

Example 7

Synthesis of Triazole Substituted Pyridoxine Analogue of Formula XIXb

Following Scheme 8, a mixture of 3-aminotriazole (142 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on silica gel the desired product XVIIIb in appreciable yields.

$^1$H nmr (CD$_3$OD, TMS): δ1.57 (6H, s), 2.36 (3H, s), 4.84 (2H, s), 4.99 (2H, s), 7.84 (1H, s, -triazole-H), 8.13 (1H, s).

The purified derivative XVIIIb (100 mg, 0.35 mmol) was dissolved in 80% aqueous acetic acid (10 mL) and heated at 60° C. for 1 hour. Purification by chromatography on silica gel gave the 3-aminotriazole pyridoxine XIXb in good yields.

$^1$H nmr (DMSO-d$_6$, TMS): δ2.34 (3H, s), 4.72 (2H, s), 5.17 (2H, s), 7.79 (1H, s, -triazole-H), 8.03 (1H, s).

Example 8

Synthesis of Triazole Substituted Pyridoxine Analogue of Formula XIXc

Following Scheme 8, a mixture of 5-aminotriazole (142 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained 0° C. for the next 30 minutes. Routine work-up gave the crude product. Purification of the crude mixture by chromatography on silica gel gave the desired product XVIIIc in appreciable yields.

$^1$H nmr (CD$_3$OD, TMS): δ1.53 (6H, s), 2.36 (3H, s), 4.84 (2H, s), 5.04 (2H, s), 7.46 (1H, s, -triazole-H), 7.68 (1H, s).

The purified derivative XVIIIc (100 mg, 0.35 mmol) was dissolved in 80% aqueous acetic acid (10 mL) and heated at 60° C. for 1 hour. Purification by chromatography on silica gel gave the 3-aminotriazole pyridoxine XIXc in good yield.

$^1$H nmr (DMSO-d$_6$, TMS): δ2.32 (3H, s), 4.75 (2H, s), 5.11 (2H, s), 7.35 (1H, s, -triazole-H), 7.58 (1H, s).

Example 9

Synthesis of Imidazole Substituted Pyridoxine Analogue of Formula XXIIa

Scheme 9

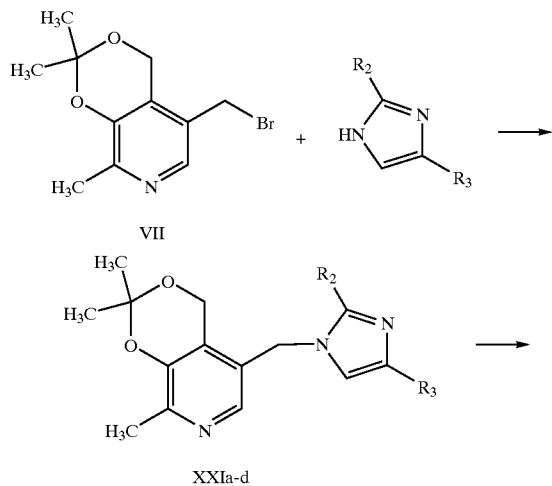

XXIa-d

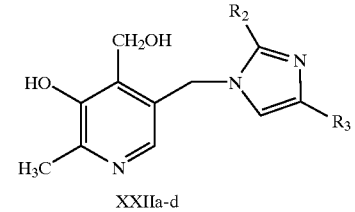

XXIIa-d

-continued a) R$_2$ = CH$_3$, R$_3$ = H
b) R$_2$ = H, R$_3$ = CH$_3$
c) R$_2$ = H, R$_3$ = NO$_2$
d) R$_2$ = NH$_2$, R$_3$ = H A mixture of 2-methylimidazole (164 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on silica gel gave the desired product XXIa in appreciable yields.

$^1$H nmr (CDCl$_3$, TMS): δ1.51 (6H, s), 2.40 (3H, s), 2.42 (3H, s, immidazole-CH$_3$), 4.50 (2H, s), 4.88 (2H, s), 6.65 (1H, s, imidazole-H), 6.93 (1H, s, imidazole-H), 7.82 (1H, s).

The purified derivative XXIa (100 mg, 0.35 mmol) was then dissolved in 80% aqueous acetic acid (10 mL) and heated at 60° C. for 1 hour. Purification by chromatography on silica gel gave the 2-methylimidazole pyridoxine XXIIa in good yield.

$^1$H nmr (DMSO-d$_6$, TMS): β2.40 (3H, s), 2.21 (3H, s, imidazole-CH$_3$), 5.11 (2H, s), 5.20 (2H, s), 6.77 (1H, s, imidazole-H), 6.92 (1H, s, imidazole-H), (2H, s), 7.47 (1H, s).

Example 10

Synthesis of Imidazole Substituted Pyridoxine Analogue of Formula XXIIb

Following Scheme 9, a mixture of 4-methylimidazole (164 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on silica gel gave the desired product XXIb in appreciable yields.

$^1$H nmr (CDCl$_3$, TMS): δ1.50 (6H, s), 2.43 (3H, s), 2.20 (3H, s, imidazole-CH$_3$), 4.54 (2H, s), 4.92 (2H, s), 6.52 (1H, s, imidazole-H), 7.42 (1H, s, imidazole-H), 7.94 (1H, s).

The purified derivative XXIb (100 mg, 0.35 mmol) was dissolved in 80% aqueous acetic acid (10 mL) and heated at 60° C. for 1 hour. Purification by chromatography on silica gel gave the 4-methylimidazole pyridoxine XXIIb in good yield.

$^1$H nmr (CDCl$_3$, TMS): δ2.20 (3H, s, imidazole-CH$_3$), 2.46 (3H, s), 4.72 (2H, s), 4.90 (2H, s), 6.48 (1H, s, imidazole-H), 7.24 (1H, s, imidazole-H), 7.84 (1H, s).

Example 11

Synthesis of Imidazole Substituted Pyridoxine Analogue of Formula XXIIc

Following Scheme 9, a mixture of 4-nitroimidazole (172 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on silica gel gave the desired product XXIc in appreciable yield.

¹H nmr (CDCl₃, TMS): δ1.52 (6H, s), 2.42 (3H, s), 4.60 (2H, s), 5.09 (2H, s), 7.46 (1H, s, imidazole-H), 7.69 (1H, s, imidazole-H), 8.01 (1H, s).

The purified derivative XXIc (110 mg, 0.35 mmol) was dissolved in 80% aqueous acetic acid (10 mL) and heated at 60° C. for 1 hour. Purification by chromatography on silica gel gave the 4-nitroimidazole pyridoxine XXIIc in good yield.

¹H nmr (DMSO-d₆, TMS): δ2.42 (3H, s), 4.74 (2H, s), 5.35 (2H, s), 7.77 (1H, s, imidazole-H), 7.95 (1H, s), 8.14 (1H, s, imidazole-H).

Example 12

Synthesis of Imidazole Substituted Pyridoxine Analogue of Formula XXIId

Following Scheme 9, a mixture of 2-aminoimidazole (132 mg, 2.00 mmol) and pulverized anhydrous potassium carbonate (2.5 g) in anhydrous acetonitrile (20 mL) was stirred at 0° C. for 15 minutes. The bromide VII (q=1) (720 mg, 2.00 mmol) in anhydrous acetonitrile (5 mL) was added to the reaction mixture which was maintained at 0° C. for the next 30 minutes. Routine work-up gave the crude product. Purification of the crude mixture by chromatography on silica gel gave the desired product XXId in appreciable yield.

¹H nmr (CD₃OD, TMS): δ1.52 (6H, s), 2.35 (3H, s), 4.68 (2H, s), 4.88 (2H, s), 6.44 (1H, s, imidazole-H), 6.53 (1H, s, imidazole-H), 7.64 (1H, s).

The purified derivative XXId (106 mg, 0.35 mmol) was then dissolved in 80% aqueous acetic acid (10 mL) and heated at 60° C. for 1 hour. Purification by chromatography on silica gel gave the 2-aminoimidazole pyridoxine XXIId in good yield.

¹H nmr (CD₃OD, TMS): δ2.15(3H, s), 4.55 (2H, s), 4.75 (2H, s), 6.24 (1H, s, imidazole-H), 6.32 (1H, s, imidazole-H), 7.23 (1H, s).

Example 13

Synthesis of Guanidine Substituted Pyridoxine Analogue of Formula XXV

Scheme 4

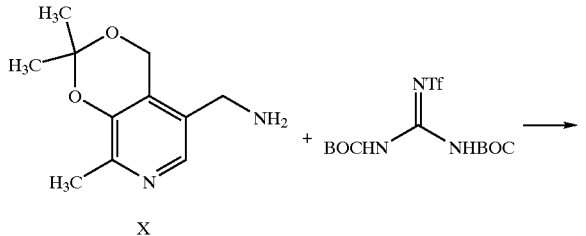

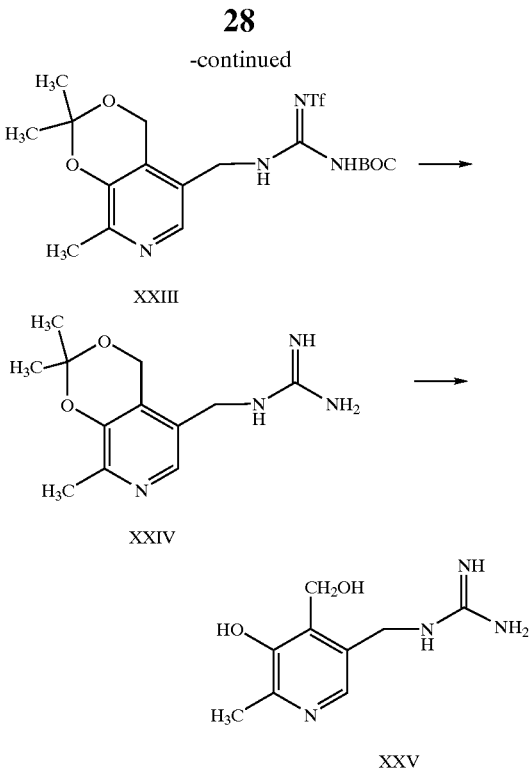

A solution of 5-aminopyridoxine derivative X (t=1) (90 mg, 0.43 mmol) in anhydrous dichloromethane (5 mL), was added a solution of triflated BOC-guanidine derivative (153.6 mg, 0.39 mmol) in anhydrous dichloromethane (5 mL) and anhydrous triethylamine (60 μL). This solution was stirred at room temperature for one hour. The reaction mixture was washed with 2M sodium bisulfite (10 mL), followed by saturated aqueous NaHCO₃. Evaporation of the dichloromethane left a residue that was purified by chromatography on silica gel to give the guanidine derivative XXIII in appreciable yield.

¹H nmr (CD₂Cl₂, TMS): δ1.46 (9H, s), 1.48 (9H, s), 1.54 (6H, s), 4.40 (2H, s), 4.88 (2H, s), 7.95 (1H, s), 8.43 (NH, s), 11.48 (NH, s).

The purified derivative XXIII (100 mg, 0.36 mmol) was then dissolved in 20% trifluoroacetic acid in anhydrous dichloromethane (10 mL) and stirred at room temperature for 1 hour. Purification of the reaction mixture gave the two products XXIV and XXV.

¹H nmr of XXIV (MeOD, TMS): δ1.64 (6H, s), 2.63 (3H, s), 4.55 (2H, s), 5.10 (2H, s), 7.52 (1H, m), 8.13 (1H, s).

¹H nmr of XXV (DMSO-d₆, TMS): δ2.54 (3H, s), 3.96 (1H, s), 4.54 (2H, d), 4.81 (2H, s), 5.96 (1H, br s, NH), 7.44 (3H, br, NH), 8.07 (1H, s).

Example 14

Synthesis of Aminotriazole Substituted Pyridoxal Analogue of Formula XXVIII

Scheme 2

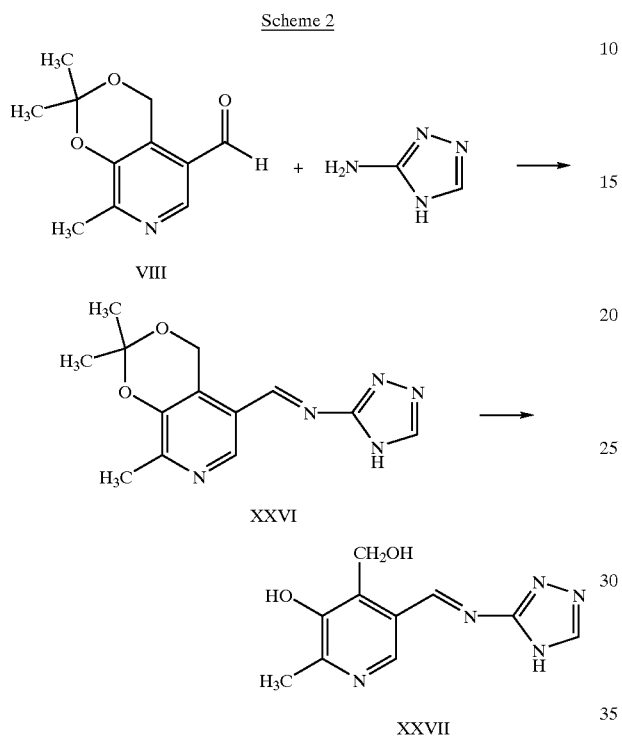

A pyridoxal derivative VIII (r=0) (400 mg, 1.91 mmol) and 3-aminotriazole (178 mg, 2.12 mmol) in anhydrous toluene (20 mL), was heated in a three neck flask, fitted with a condenser and a Dean Stark trap, at 100° C. for 24 hours. Routine workup gave the crude product, which was then purified by chromatography on silica gel to give the protected triazoline derivative XVI in modest yields.

$^1$H nmr (CD$_3$OD, TMS): δ1.58 (6H, s), 2.46 (3H, s), 3.31(1H, s), 5.31 (2H, s), 8.41 (1H, s), 9.23 (1H, s, -triazoline CH).

The fully protected pyridoxine derivative XXVI (206 mg, 0.88 mmol) was dissolved in 80% aqueous acetic acid (10 mL) and heated at 60° C. for 1 hour. Purification by chromatography on silica gel gave the triazoline substituted pyridoxine XXVII in good yield.

$^1$H nmr (CD$_3$OD, TMS: δ2.46 (3H, s), 5.10 (2H, m), 6.78 (1H, s, -triazoline CH), 7.92 (1H, s).

Example 15

Synthesis of Imidazoline Substituted Pyridoxine Analogue of Formula XXIX

Scheme 2

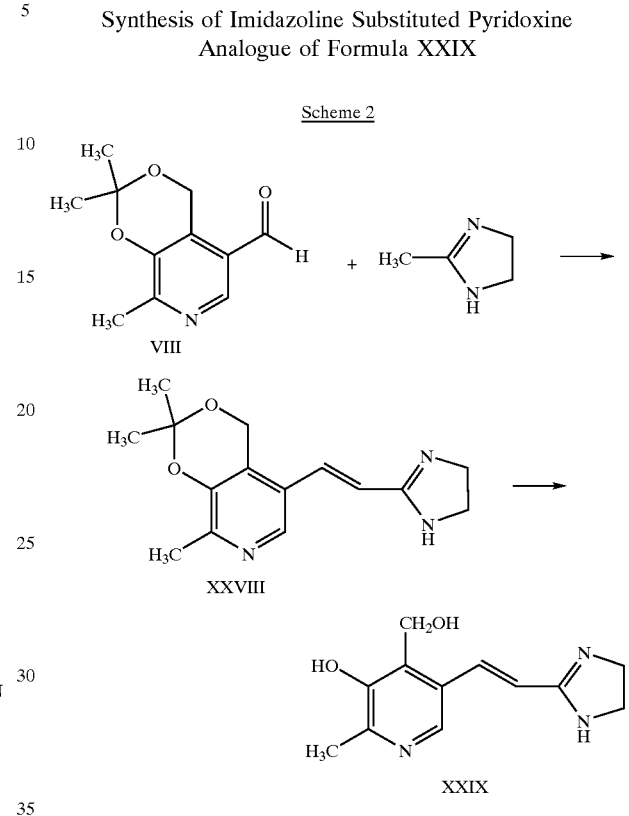

A pyridoxal derivative VIII (r=0) (2.07 g, 10.00 mmol) and 2-methylimidazoline (1.68 g, 20.00 mmol) in anhydrous toluene (50 mL), was heated in a three neck flask, fitted with a condenser and a Dean Stark trap, at 100° C. for 24 hours. Routine workup gave the crude product, which was then purified by chromatography on silica gel to give the protected imidazoline derivative XXVIII in modest yields.

$^1$H nmr (CD$_3$OD, TMS): δ1.56 (6H, s), 2.38 (3H, s), 3.76 (4H, s), 4.98 (2H, s), 6.63 (1H, s, vinylic CH), 7.26 (1H, s, vinylic-CH), 8.20 (1H, s).

The fully protected pyridoxine derivative XXVIII (100 mg, 0.43 mmol) was dissolved in 80% aqueous acetic acid (5 mL) and heated at 60° C. for 1 hour. Purification by chromatography on silica gel gave the imidazoline XXIX in good yield.

$^1$H nmr (CD$_3$OD, TMS): δ2.14 (3H, s), 3.09 (2H, s), 3.56 (4H, s), 4.74 (1H, s, vinylic CH), 4.87 (1H, s, vinylic-CH), 5.24 (1H, d, NH) 7.26 (1H, s).

Example 16

Synthesis of Imidazole Substituted Pyridoxine Analogue of Formula XXXI

Scheme 11

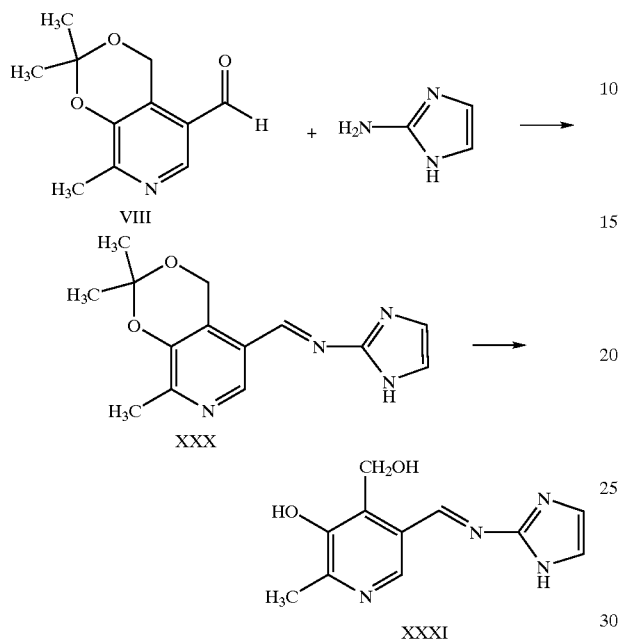

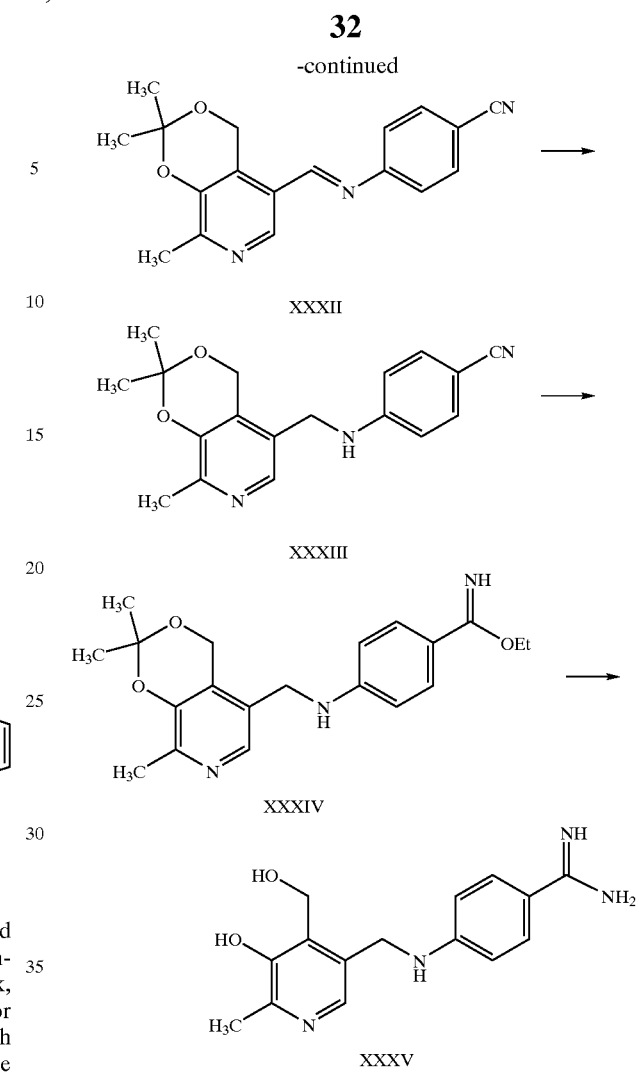

Pyridoxal derivative VIII (r=0) (800 mg, 3.82 mmol) and 2-aminoimidazole (346 mg, 4.2 mmol) in anhydrous dimethyl sulfoxide (75 mL), was heated in a three neck flask, fitted with a condenser and a Dean Stark trap, at 100° C. for three days. Routine workup gave the crude product, which was then purified by chromatography on silica gel to give the protected cyclic guanidine derivative XXX in modest yield.

$^1$H nmr (MeOD, TMS): δ1.58 (6H, s) 2.49 (3H, s), 5.26 (2H, s), 7.07 (2H, s imidazole-H), 8.49 (1H, s), 9.27 (1H, s-vinylic H).

The protected pyridoxine derivative XXX (110 mg, 0.44 mmol) was dissolved in 80% aqueous acetic acid (5 mL) and heated at 60° C. for 1 hour. Purification by chromatography on silica gel gave the cyclic guanidine XXXI in good yield.

$^1$H nmr (MeOD, TMS): δ2.45 (3H, s), 4.96 (2H, m), 5.12 (2H, dd), 6.43 (1H, d), 7.92 (1H, s).

Example 17

Synthesis of Aminophenylamidine Substituted Pyridoxine Analogue of Formula XXXV Scheme 3

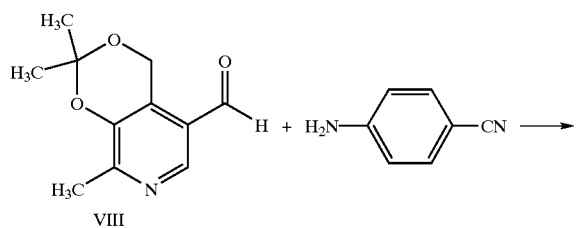

In a 250 mL three-necked flask fitted with a condenser and a Dean stark trap was added protected pyridoxine aldehyde VIII (r=0) (3.31 g, 16 mmol), 4-cyano aniline (1.89 g, 15.9 mmol), p-toluenesulfonic acid (0.3 g, 1.6 mmol) and dry benzene (60 mL). The reaction mixture was then heated to reflux for 16 hours. The reaction mixture was then washed with 2N NaOH (5 mL) followed by brine (10 mL) and the organic layer dried with anhydrous Na$_2$SO$_4$. Removal of the solvent gave the crude product, which was purified by silica gel column chromatography, using the eluant 100:1/ CH$_2$Cl$_2$:2M NH$_3$-MeOH. XXXII was obtained as a pure yellow solid. (2.98 g, 61% yield).

$^1$HNMR (CDCl$_3$) δ1.58 (s 6H) 2.49 (s, 3H) 5.27 (s, 2H) 7.20 (d, 2H) 7.68 (d, 2H) 8.31 (s, 1H) 8.44 (s, 1H).

The Schiff base XXXII (358 mg, 1.0 mmol) was dissolved in HOAc (5 mL) and the solution cooled to 0° C. Sodium borohydride (57 mg, 1.5 mmol) was added in portions, while stirring continued for 10 minutes at 0° C., and then at room temperature for another 10 minutes. The reaction was quenched by adding 5 N NaOH (1.8 mL) to bring the pH of the solution to 9. The product was then extracted with diethyl ether (2×10 mL) and dried over anhydrous Na$_2$SO$_4$. Evaporation of the solvent, followed by purification on silica gel column chromatography in EtOAc: Hexanes/1:1 gave XXXIII as a pale yellow solid (300 mg, 90%)

$^1$HNMR (CDCl$_3$) δ1.54 (s, 6H), 2.40 (s, 3H) 4.20 (s, 2H) 4.36 (br, 1H) 4.84 (s, 2H) 6.62 (d, 2H) 7.45 (d, 2H) 8.00 (s, 1H).

Into a solution of the amine XXXIII (81 mg, 0.3 mmol) in ethanol (6 mL) at 0° C. was bubbled hydrogen chloride gas (dry) for 30 min. The reaction mixture was slowly allowed to reach the room temperature and then stirred at this temperature for 16 hours. The solution was again cooled to 0° C., and then degassed by bubbling $N_2$ through it for 2 h. On evaporation of the solvent XXXIV was obtained as a light yellow solid.

$^1$HNMR (MeOD) δ1.57 (t, 3H) 2.64 (s, 3H) 4.54 (q, 2H) 4.65 (s, 2H) 5.14 (s, 2H) 6.82 (d, 2H) 7.89 (d, 2H) 8.00 (s, 1H).

In a sealed high pressure flask containing the crude compound XXXIV (106 mg, 0.3 mmol) was added 2 M $NH_3$-MeOH (10 mL) and the mixture cooled to −78° C., and stirred at this temperature for 15 minutes. The reaction mixture was gradually warmed to rt, and then heated to 80° C. for 2 h. The reaction mixture was again cooled to −78° C. and then the sealed flask was opened. The solution was then transferred to a round-bottomed flask and the solvent evaporated to dryness. Purification on silica gel column using 100:20:1/$CH_2Cl_2$:MeOH:H2O as eluent gave XXXV as white solid (88 mg, 82%).

$^1$HNMR (MeOD) δ2.43 (s, 3H) 4.45 (s, 2H) 4.96 (s, 2H) 6.78 (d, 2H) 7.64 (d, 2H) 7.84 (s, 1H).

Example 18

Synthesis of Aminophenylamidine Substituted Pyridoxine Analogue of Formula XL

Scheme 12

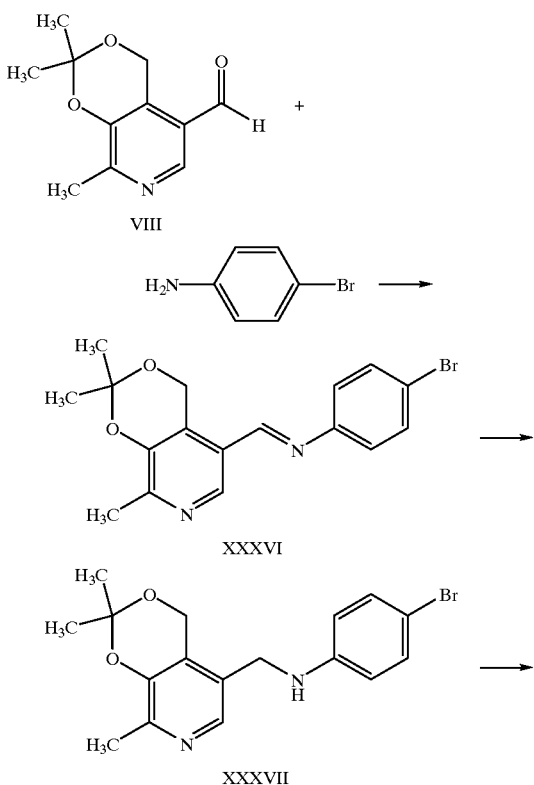

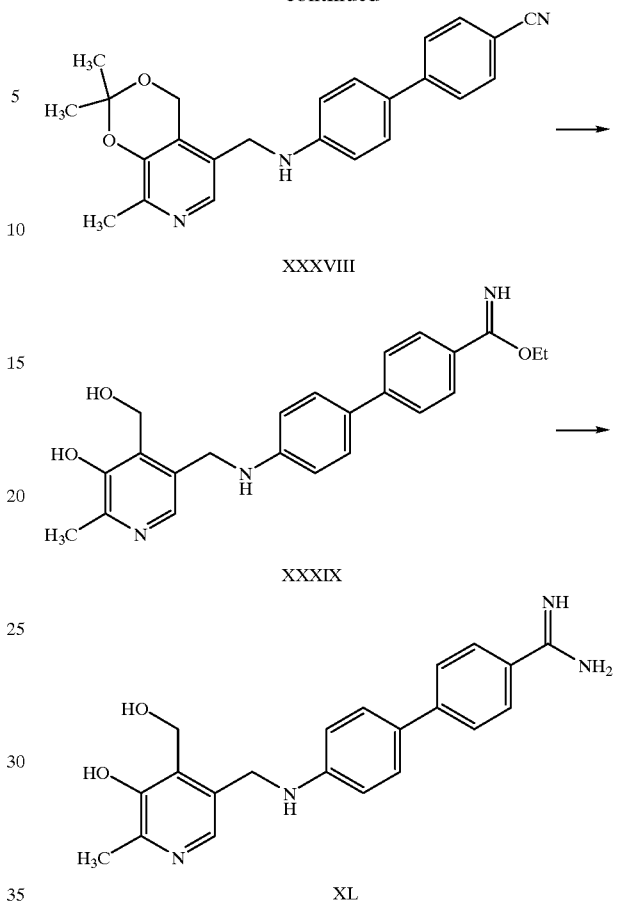

The procedure for the preparation of XXXVI was similar to that used for the synthesis of compound XXXIIII. The crude product, XXXVI, was an auburn solid and was used in the next step without purification.

$^1$HNMR (CDCl$_3$) δ1.59 (s, 6H) 2.49 (s, 3H) 5.30 (s, 2H) 7.06 (d, 2H) 7.51 (d, 2H) 8.30 (s, 1H) 8.47 (s, 1H).

The procedure for the preparation of XXXVII was similar to that used for the synthesis of compound XXXIII. The crude product, XXXVII, was purified by silica gel column, using 5:1:1.5/$CH_2Cl_2$:MeOH:H$_2$O, as eluant to give a yield white solid. (66% yield).

$^1$HNMR (CDCl$_3$) δ1.55 (s, 6H) 2.41 (s, 3H) 3.68 (br, 1H) 4.12 (d, 2H) 4.87 (s, 2H) 6.51 (d, 2H) 7.27 (d, 2H) 8.01 (s, 1H).

Compound XXXVII (665 mg, 1.83 mmol) was dissolved in diglyme (15 mL), followed by the addition of Pd (PPh$_3$)$_4$ (63 mg, 0.05 mmol). The mixture was stirred for 10 min, and then p-cyanophenylboronic acid (269 mg, 2.01 mmol) was added to the reaction mixture followed by sodium bicarbonate (461 mg in 8 mL H$_2$O, 5.49 mmol). The reaction mixture was heated to 95° C. in an oil bath for 5 min, and then stirred at room temperature for 1.5 h. On evaporation of the solvent a dark purple crude product, XXXVIII, was obtained which was purified by silica gel column chromatography (1:1/ EtOAc:Hexane, 32% yield.).

$^1$H NMR (CDCl$_3$) δ1.56 (s, 6H) 2.42 (s, 3H) 3.96 (br, 1H) 4.22 (d, 2H) 4.91 (s, 2H) 6.72 (d, 2H) 7.47 (d, 2H) 7.65 (q, 4H) 8.06 (s, 1H).

The syntheses of compound XXXIX and XL were accomplished by the procedures outlined for compounds XXXIV and XXXV. Overall yield of XL was 63% for the two steps.

¹HNMR (XXXIX) (MeOD) δ1.62 (t, 3H) 2.62 (s, 3H) 4.56 (s, 2H) 4.63 (q, 2H) 5.17 (s, 2H) 6.78 (d, 2H) 7.60 (d, 2H) 7.83 (d, 2H) 8.02 (s, 1H) 8.05 (d, 2H).

¹HNMR (XL) (MeOD) δ2.43 (s, 3H) 4.39 (s, 2H) 4.98 (s, 2H) 6.76 (d, 2H) 7.54 (d, 2H) 7.80 (m, 4H) 7.89 (s, 1H).

Example 19

Synthesis of Arylurea and Arylthiourea Substituted Pyridoxine Analogues of Formulas XLIII and XLIV Scheme 5

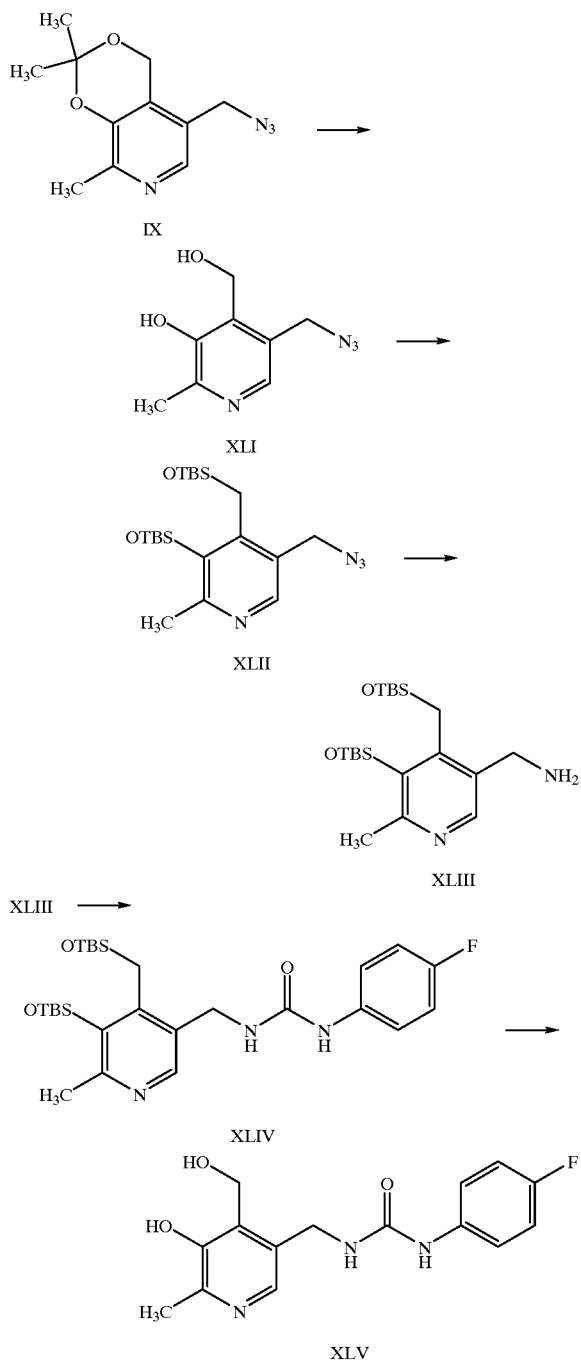

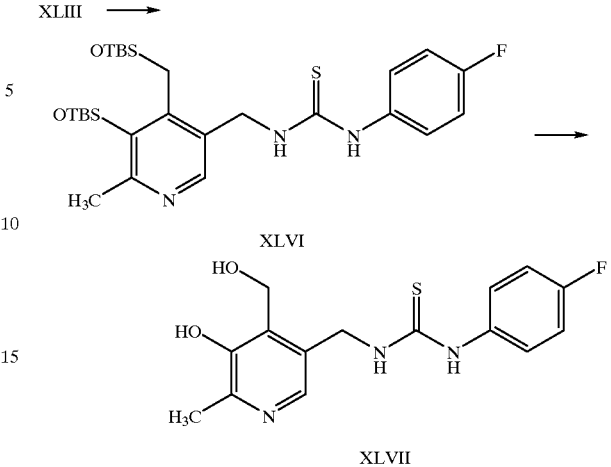

The azide IX (t=1) (790 mg, 3.4 mmol) was dissolved in 80% aqueous HOAc (40 mL) and heated at 60° C. for 16 hours, to hydrolyze the isopropylidene group. Co-distillation with toluene to remove acetic acid gave the crude product, which was purified by silica gel column chromatography. (1:1→4:1/EtOAc:Hexane), giving XLI as a white solid (410 mg, 63% yield.)

¹H NMR (MeOD) δ2.43 (s, 3H) 4.42 (s, 2H) 4.92 (s, 2H) 7.86 (s, 1H).

To the de-blocked azide XLI (388 mg, 2.0 mmol) in dry DMF (10 mL) was added imidazole (545 mg, 8.8 mmol) and TBDPSiCl (1.2 ml, 4.4 mmol). The reaction mixture was then heated to 50° C. and kept stirring for overnight. The reaction was then cooled to room temperature, and then extracted with diethyl ether (2×25 mL), followed by washing the ether extract by water (2×10 mL) and brine (1×10 mL). The ethereal solution was then dried over MgSO₄ and solvent evaporated to dryness to give XLII as a white solid. (1.3 g, 97% yield).

¹H NMR (CDCl₃) δ0.87 (s, 9H) 0.96 (s, 9H) 2.15 (s, 3H) 4.49 (s, 2H) 4.52 (s, 2H) 7.38 (m, 20H) 8.03 (s, 1H).

To the compound XLII (1.3 g, 1.94 mmol) dissolved in methanol (20 mL) was added Lindlar catalyst (600 mg) and the mixture hydrogenated under a stream H₂ for 1.5 hours to complete the reaction. The routine work up and purification gave the amine XLIII (0.95 g, 76%).

¹H NMR (CDCl₃) δ0.83 (s, 9H) 0.96 (s, 9H) 1.51 (br, 2H) 2.11 (s, 3H) 3.89 (s, 2H) 4.57 (s, 2H) 7.33 (m, 20) 8.09 (s, 1H).

A mixture of XLIII (645 mg, 1.0 mmol) and the 4-fluorophenylisocyanate (0.12 mL, 1.0 mmol) in dry toluene (10 mL) was refluxed for 16 hours. After the removal of the solvent, the crude product was purified by silica gel column chromatography, using 100:1→100:2/CH₂Cl₂:95% EtOH as eluent, giving XLIV a white solid (619 mg, 79%).

¹H NMR (CDCl₃) δ0.87 (s, 9H) 0.97 (s, 9H) 2.13 (s, 3H) 4.87 (d, 2H) 4.62 (s, 2H) 5.05 (br, 1H) 6.15 (br, 1H) 7.33 (m, 20H) 8.19 (s, 1H). ¹⁹F NMR CDCl₃ δ−120.40 (s).

To a solution of XLIV (391 mg, 0.5 mmol) in dry THF (10 ml) was added TBAF (0.32 ml, 2.2 mmol) and stirred at room temperature for 16 hours. Removal of the solvent followed by purification by silica gel column chromatography using 20:1→10:1/CH₂Cl₂:MeOH, as eluent gave XLV as a white solid. (135 mg, 89%).

¹H NMR (MeOD) δ2.40 (s, 3H) 4.39 (s, 2H) 4.94 (s, 2H) 6.98 (m, 2H) 7.34 (m, 2H) 8.78 (s, 1H). ¹⁹F NMR (MeOD) δ−123.51 (m).

The syntheses of compounds XLVI and XLVII followed the procedure outlined for XLIV and XLV using 4-fluorophenylthioisocyanate in place of 4-fluorophenylisocyanate. Yields obtained were 65% for XLVI and 60% for XLVII.

$^1$H NMR (XLVI) (CDCl$_3$) δ0.82 (s, 9H) 0.88 (s, 9H) 2.09 (s, 3H) 4.52 (s, 2H) 5.00 (d, 2H) 5.29 (s, 1H) 6.36 (t, 1H) 7.33 (m, 20H) 8.02 (s, 1H). $^{19}$F NMR (CDCl$_3$) δ−113.42 (s).

$^1$H NMR (XLVII) (MeOD) δ2.41 (s, 3H) 3.07 (m, 1H) 3.54 (m, 1H) 4.91 (s, 2H) 7.09 (t, 2H) 7.32 (q, 2H) 7.89 (s, 1H). $^{19}$F NMR (MeOD) δ−118.80 (m).

Example 20

Inhibition of Platelet Aggregation

Platelet rich plasma (PRP) was obtained by drawing whole blood into sodium citrate tubes (3.2%) and centrifuging at 700 rpm for 10 minutes. Platelet poor plasma (PPP) was obtained by centrifuging the remainder of the sample until the platelets were removed (3200 rpm for 10 minutes). The PRP was adjusted to a count of 280×10$^9$/L using a mixture of PRP and PPP. The incubation mixture consisted of 200 μL of platelets and 25 μL of the appropriate compound (18 mM stock for a final concentration of 2 mM and 4.5 mM stock for a final concentration of 500 μM), rendering an approximate final platelet count in the incubation mixture of 250×10$^9$/L. After incubation (30 minutes at room temperature, the cuvettes were incubated for 3 minutes at 37° C., transferred to the mixing wells and after the baselines transmittances were measured in an aggregometer (Chrono-Log 4), 25 μL of agonist was added to give a final concentration of 4 μM ADP, 1 g/mL collagen, 5 μg/mL collagen or 12 μM thrombin receptor activating peptide (TRAP). Final transmittances were then measured in the aggregometer (lower percent transmittance represents higher aggregation). Agonists concentrations were chosen based on previous experience that indicated that these were the smallest concentrations that would give the full extent of aggregation in the normal population. Table V gives the results of the extent of aggregation for several compounds as percentage amplitude read directly from the aggregometer.

TABLE I

| Extent of aggregation as a percentage amplitude, read directly from the aggregometer. | | | | | |
|---|---|---|---|---|---|
| Compound Tested | 5 μg/mL collagen | 1 μg/mL collagen | 4 μM ADP | 12 μM TRAP | Diluent of Compound |
| Saline Control | 82% | 87% | 83% | 93% | |
| DMSO Control | 85% | 86% | 55% | 88% | |
| XL 2 mM | 5% | 4% | 4% | 4% | saline |
| XL 500 μM | 52% | 4% | 9% | 3% | saline |
| XLVII 2 mM | 49% | 30% | 31% | 42% | 20% DMSO in saline |
| XXXV 2 mM | 67% | 79% | 15% | 11% | saline |
| XXXV 500 μM | 75% | 83% | 70% | 90% | saline |
| XXIIb 2 mM | 77% | 32% | 46% | 84% | 1 part DMSO 1 part saline |
| XXIIb 500 μM | 82% | 79% | 59% | 91% | 1 part DMSO 1 part saline |

TABLE I-continued

| Extent of aggregation as a percentage amplitude, read directly from the aggregometer. | | | | | |
|---|---|---|---|---|---|
| Compound Tested | 5 μg/mL collagen | 1 μg/mL collagen | 4 μM ADP | 12 μM TRAP | Diluent of Compound |
| PLP 2 mM | 89% | 84% | 16% | 91% | saline |
| PLP 500 μM | 87% | 89% | 69% | 90% | saline |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

I claim:
1. A compound of Formula V:

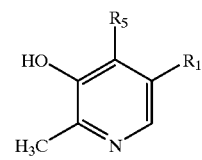

or a pharmaceutically acceptable acid addition salt thereof, wherein:

$R_5$ is CH$_2$OH or CHO;

$R_1$ is

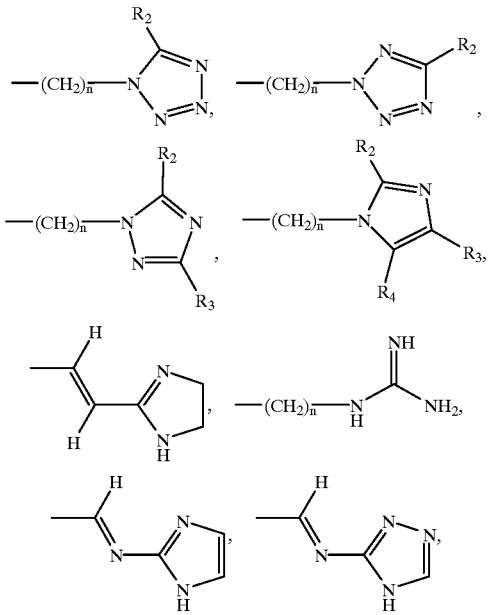

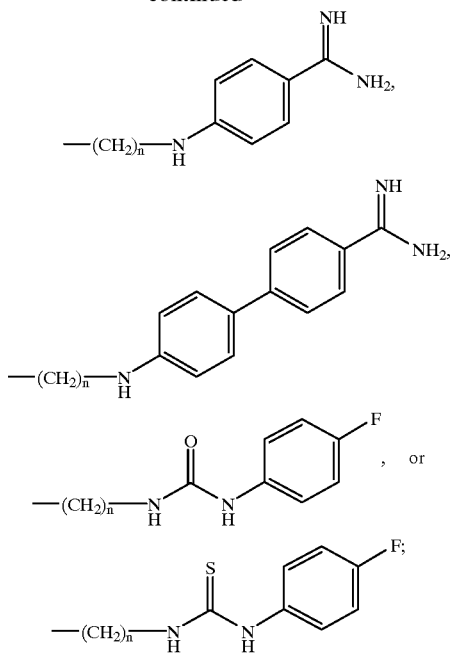

n is an integer of 1 to 5;
$R_2$, $R_3$, and $R_4$ are each independently
   hydrogen;
   alkyl;
   aryl or biaryl,
      wherein the aryl or biaryl can be substituted with a cyano, alkyl, alkoxy, amino, hydroxy, halo, nitro, or alkanoyloxy;
   amino;
   acylamino;
   anilino,
      wherein the aniline ring can be substituted with a cyano, alkyl, alkoxy, amino, hydroxy, halo, nitro, or alkanoyloxy;
   nitro; or
   guanidino.

2. The compound of claim 1 wherein, $R_1$ is

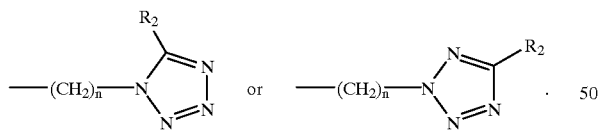

3. The compound of claim 2, wherein $R_2$ is hydrogen, alkyl, or amino.

4. The compound of claim 1, wherein $R_1$ is

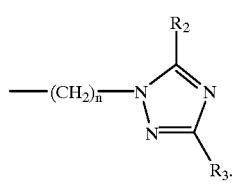

5. The compound of claim 4, wherein $R_2$ and $R_3$ are each independently hydrogen, alkyl, amino, or nitro.

6. The compound of claim 1, wherein $R_1$ is

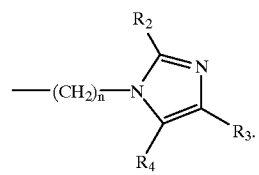

7. The compound of claim 6, wherein $R_2$, $R_3$, and $R_4$ are independently hydrogen, alkyl, or amino.

8. The compound of claim 6, wherein $R_2$ is hydrogen, $R_3$ is methyl, and $R_4$ is hydrogen.

9. The compound of claim 1, wherein $R_1$ is

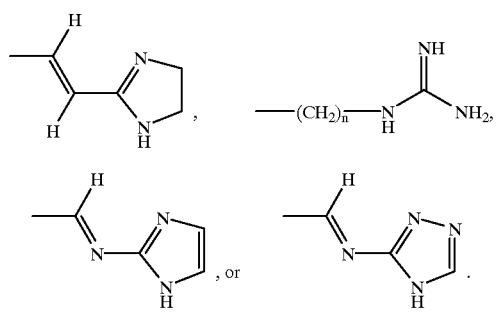

10. The compound of claim 1, wherein $R_1$ is

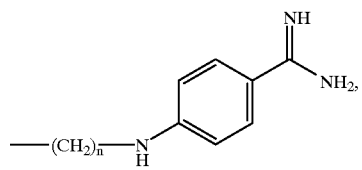

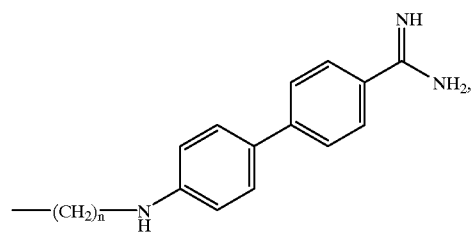

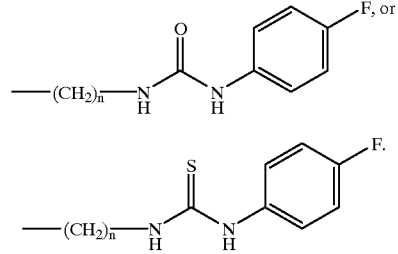

11. The compound of claim 1, wherein $R_1$ is

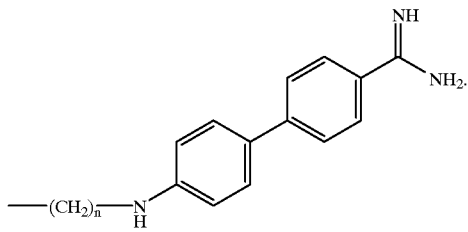

12. A pharmaceutical composition comprising: a pharmaceutically acceptable carrier and a therapeutically effective amount of a compound according to claim 1.

13. The pharmaceutical composition of claim 12, wherein the pharmaceutical composition is in a form suitable for enteral or parenteral administration.

14. A method of treating a cardiovascular or related disease comprising administering to a mammal a therapeutically effective amount of a compound according to claim 1 in a unit dosage form.

15. The method of claim 14, wherein said therapeutically effective amount is in a range of about 0.5–100 mg/kg per day of the mammal's body weight.

16. The method of claim 14, wherein said compound is administered enterally or parenterally.

17. The method of claim 14, further comprising administering concurrently another therapeutic agent.

18. The method of claim 14, wherein the cardiovascular or related disease is selected from the group consisting of cerebral ischemia, cerebral hemorrhage, ischemic stroke, and hemorrhagic stroke.

19. The method of claim 14, wherein the cardiovascular or related disease is hypertension.

20. The method of claim 19, further comprising administering concurrently a thereapeutic cardiovascular compound selected from the group consisting of an angiotensin converting enzyme inhibitor, a calcium channel blocker, a β-adrenergic receptor antagonist, a vasodilator, a diuretic, an α-adrenergic receptor antagonist, and a mixture thereof.

21. The method of claim 14, wherein the cardiovascular or related disease is myocardial infarction.

22. The method of claim 21, further comprising administering concurrently a therapeutic cardiovascular compound selected from the group consisting of an angiotensin converting enzyme inhibitor, a calcium channel blocker, an antithromblytic agent, a β-adrenergic receptor antagonist, a diuretic, an α-adrenergic receptor antagonist, and a mixture thereof.

23. The method of claim 14, wherein the cardiovascular or related disease is ischemia reperfusion injury.

24. The method of claim 23, further comprising administering concurrently a therapeutic cardiovascular compound selected from the group consisting of an angiotensin converting enzyme inhibitor, an angiotensin II receptor antagonist, a calcium channel blocker, and a mixture thereof.

25. The method of claim 14, wherein the cardiovascular or related disease is myocardial ischemia.

26. The method of claim 25, further comprising administering concurrently a therapeutic cardiovascular compound selected from the group consisting of an angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, and a mixture thereof.

27. The method of claim 14, wherein the cardiovascular or related disease is congestive heart failure.

28. The method of claim 27, further comprising administering concurrently with a therapeutic cardiovascular compound selected from the group consisting of an angiotensin converting enzyme inhibitor, an angiotensin II receptor antagonist, a calcium channel blocker, a vasodilator, a diuretic, and a mixture thereof.

29. The method of claim 14, wherein the cardiovascular or related disease is arrhythmia.

30. The method of claim 29, further comprising administering concurrently a therapeutic cardiovascular compound selected from the group consisting of a calcium channel blocker, a β-adrenergic receptor antagonist, and a mixture thereof.

31. The method of claim 14, wherein the cardiovascular or related disease is a blood coagulation disorder.

32. The method of claim 31, further comprising administrating concurrently an antithrombolytic agent.

33. The method of claim 31, wherein the cardiovascular or related disease is cardiac hypertrophy.

34. The method of claim 33, further comprising administering concurrently a therapeutic cardiovascular compound selected from the group consisting of an angiotensin converting enzyme inhibitor, an angiotensin II receptor antagonist, a calcium channel blocker, and a mixture thereof.

35. The method of claim 14, wherein the cardiovascular or related disease arises from thrombotic and prothrombotic states in which the coagulation cascade is activated.

36. The method of claim 35, wherein the disease is deep vein thrombosis, disseminated intravascular coagulopathy, or pulmonary embolism.

37. The method of claim 14, wherein the cardiovascular or related disease is platelet aggregation.

38. A method of preparing a compound according to claim 1 wherein $R_1$ is

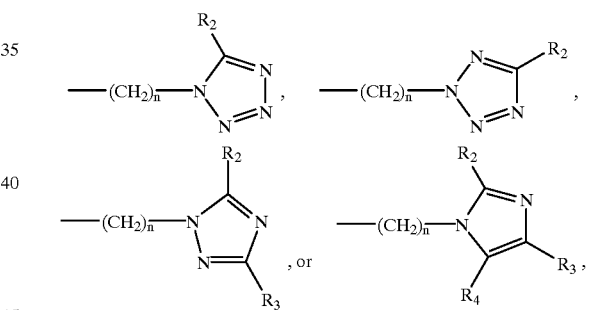

the method comprising:

(a) choosing a precursor compound of Formula VII:

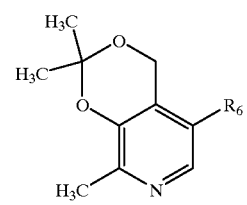

VII wherein $R_6$ is $(CH_2)_p Br$ with q=1 to 5;

(b) reacting the precursor with a substituted or unsubstituted tetrazole, a substituted or unsubstituted triazole, or a substituted or unsubstituted imidazole; and (c) hydrolyzing to remove the isopropylidene group.

39. A method of preparing a compound according to claim 1, wherein $R_1$ is

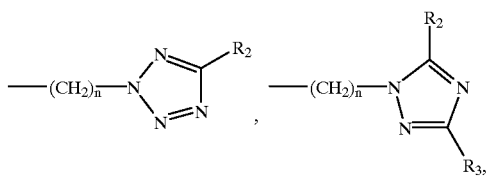

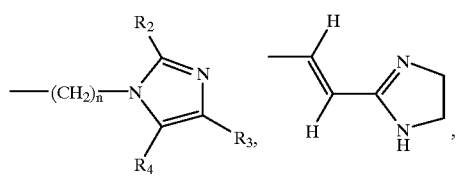

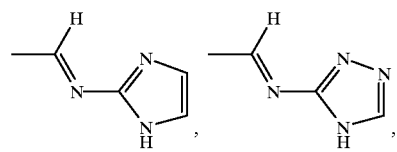

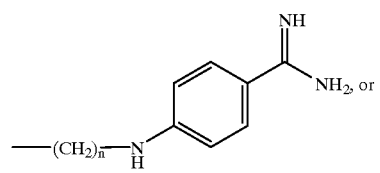

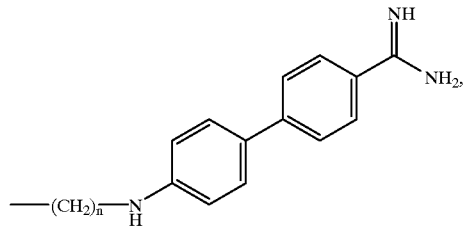

the method comprising:

(a) choosing a precursor compound of Formula VIII:

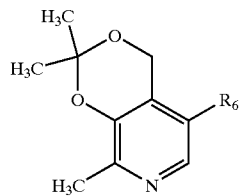

VIII wherein $R_6$ is $(CH_2)_r CHO$ with r=0 to 4;

(b) reacting the precursor with a substituted or unsubstituted triazole, a substituted or unsubstituted imidazole, or a substituted or unsubstituted aniline compound; and (c) hydrolyzing to remove the isopropylidene group.

40. A method of preparing a compound according to claim 1 wherein $R_1$ is

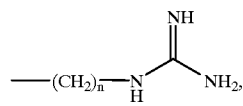

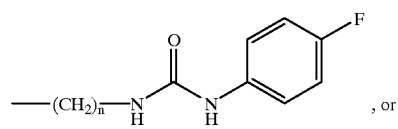, or

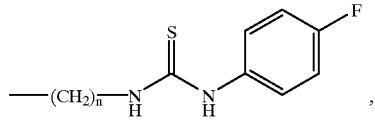, the method comprising:

(a) choosing a precursor compound of Formula IX:

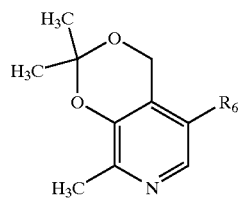

IX wherein $R_6$ is $(CH_2)_s N_3$ where s=1 to 5;

(b) reducing the azide group to form and amine derivative;

(c) reacting the amine derivative with a guanidine, substituted or unsubstituted aromatic isocyanate, or a substituted or unsubstituted aromatic thioisocyanate; and (c) hydrolyzing to remove the isopropylidene group.

41. A method of preparing a compound according to claim 1 wherein $R_1$ is

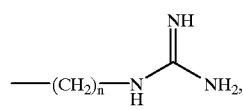

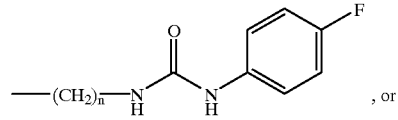, or

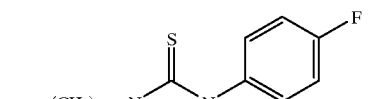, the method comprising:

(a) choosing a precursor compound of Formula X:
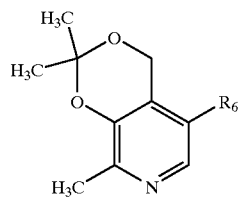
X
wherein $R_6$ is $(CH_2)_tNH_2$ where t=1 to 5;
(b) reacting the precursor with a protected guanidine derivative, a substituted or unsubstituted aromatic isocyanate, or a substituted or unsubstituted aromatic thioisocyanate; and
(c) hydrolyzing to remove the isopropylidene group.
* * * * *